US012257121B2

(12) United States Patent
Orrego

(10) Patent No.: US 12,257,121 B2
(45) Date of Patent: Mar. 25, 2025

(54) SMART COMPOSITE WITH ANTIBIOFILM, MINERALIZING, AND ANTIINFECTION THERAPEUTIC EFFECTS

(71) Applicant: Temple University—Of The Commonwealth System of Higher Education, Philadelphia, PA (US)

(72) Inventor: Santiago Orrego, Philadelphia, PA (US)

(73) Assignee: Temple University—Of The Commonwealth System of Higher Education

( * ) Notice: Subject to any disclaimer, the term of this patent is extended or adjusted under 35 U.S.C. 154(b) by 578 days.

(21) Appl. No.: 17/442,357

(22) PCT Filed: Mar. 26, 2020

(86) PCT No.: PCT/US2020/024951
§ 371 (c)(1),
(2) Date: Sep. 23, 2021

(87) PCT Pub. No.: WO2020/198468
PCT Pub. Date: Oct. 1, 2020

(65) Prior Publication Data
US 2022/0160464 A1    May 26, 2022

Related U.S. Application Data

(60) Provisional application No. 62/823,833, filed on Mar. 26, 2019.

(51) Int. Cl.
*A61C 5/40*    (2017.01)
*A61C 8/00*    (2006.01)
(Continued)

(52) U.S. Cl.
CPC .............. *A61C 5/40* (2017.02); *A61C 8/0007* (2013.01); *A61C 8/0013* (2013.01); *A61K 6/15* (2020.01); *A61K 6/20* (2020.01); *A61K 6/60* (2020.01); *A61L 27/06* (2013.01); *A61L 27/306* (2013.01); *A61L 27/446* (2013.01); *A61L 27/54* (2013.01); *A61L 2300/404* (2013.01);
(Continued)

(58) Field of Classification Search
CPC combination set(s) only.
See application file for complete search history.

(56) References Cited

U.S. PATENT DOCUMENTS 4,365,359 A * 12/1982 Raab ...................... A61L 27/28
427/388.5
5,507,814 A *  4/1996 Gilbert ................ A61L 24/0094
606/76
(Continued)

FOREIGN PATENT DOCUMENTS

WO    WO-2005118744 A1 * 12/2005 ............. A61C 13/30

*Primary Examiner* — Peter A Salamon
(74) *Attorney, Agent, or Firm* — Riverside Law LLP

(57) ABSTRACT

The present invention provides novel multi-functional (e.g., repelling biofilms, promoting formation of minerals, and
(Continued)

having anti-infection properties) biocomposites and methods of use thereof. In various embodiments, the present invention also provides method for simultaneously treating biofilms, promoting mineralization, treating infection, or any combination thereof.

12 Claims, 27 Drawing Sheets

(51) Int. Cl.
| | | |
|---|---|---|
| *A61C 8/02* | (2006.01) |
| *A61K 6/15* | (2020.01) |
| *A61K 6/20* | (2020.01) |
| *A61K 6/60* | (2020.01) |
| *A61L 27/06* | (2006.01) |
| *A61L 27/30* | (2006.01) |
| *A61L 27/44* | (2006.01) |
| *A61L 27/54* | (2006.01) |
| *B82Y 5/00* | (2011.01) |
| *B82Y 40/00* | (2011.01) |

(52) U.S. Cl.
CPC ....... *A61L 2400/12* (2013.01); *A61L 2430/12* (2013.01); *B82Y 5/00* (2013.01); *B82Y 40/00* (2013.01)

(56) References Cited

U.S. PATENT DOCUMENTS

| | | | | |
|---|---|---|---|---|
| 5,874,123 | A * | 2/1999 | Park | A61F 2/30767 427/322 |
| 6,075,067 | A * | 6/2000 | Lidgren | A61L 27/46 524/436 |
| 6,080,801 | A * | 6/2000 | Draenert | A61L 24/0073 523/205 |
| 7,674,477 | B1 * | 3/2010 | Schmid | A61F 2/28 604/890.1 |
| 2012/0295448 | A1 * | 11/2012 | Miller | B82Y 40/00 977/773 |
| 2013/0144400 | A1 * | 6/2013 | Day | A61L 27/446 623/23.72 |
| 2013/0178947 | A1 * | 7/2013 | Monaghan | A61L 27/04 623/23.55 |
| 2015/0134061 | A1 * | 5/2015 | Friis | H10N 30/852 264/439 |
| 2016/0209124 | A1 * | 7/2016 | Da Silvaa | C01B 32/16 |

* cited by examiner

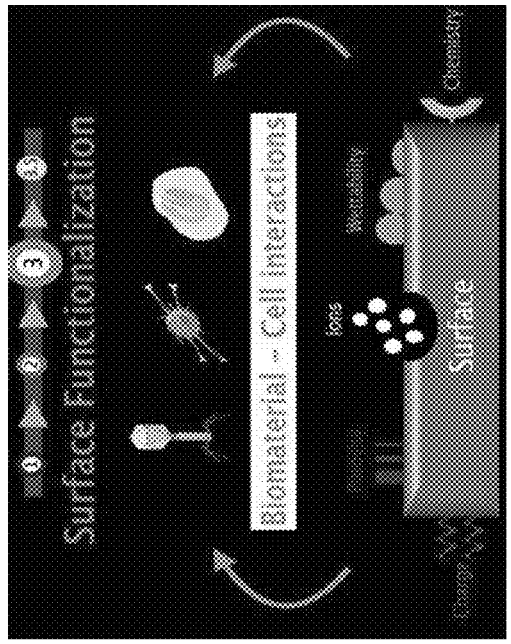
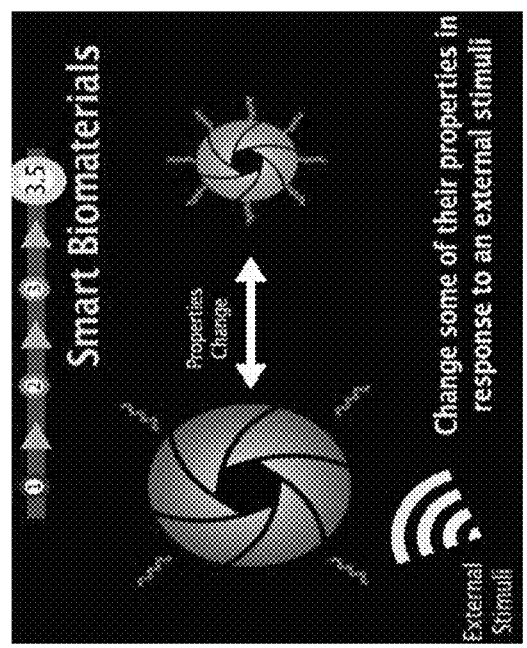
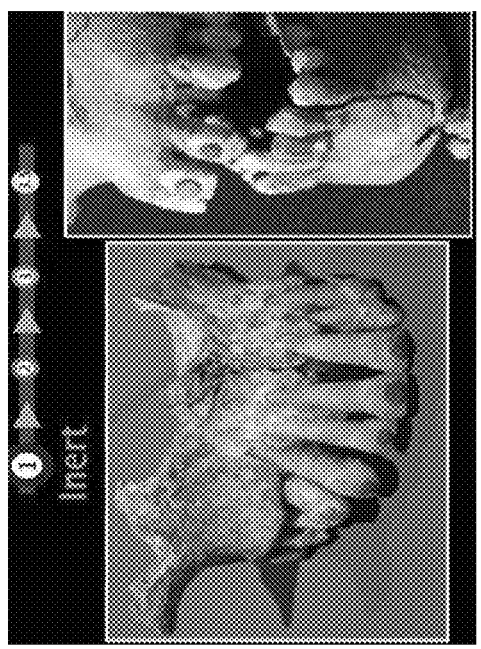
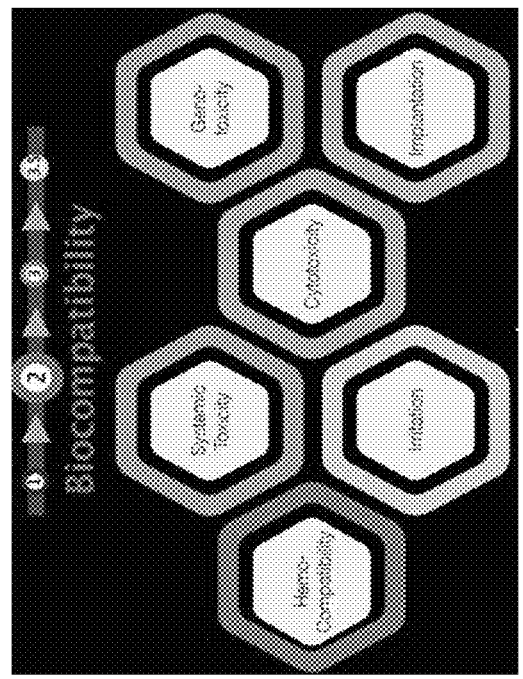
Figure 3

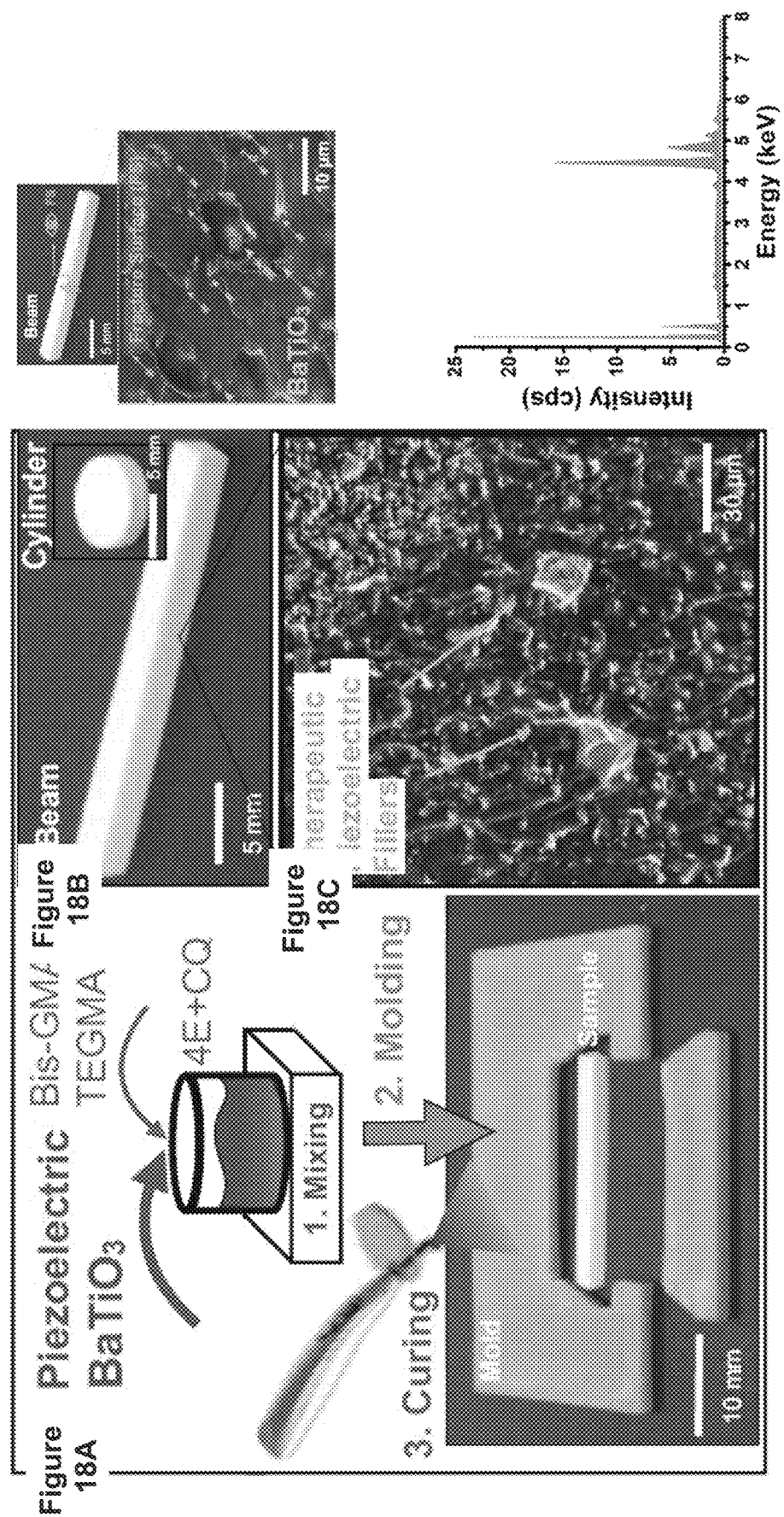

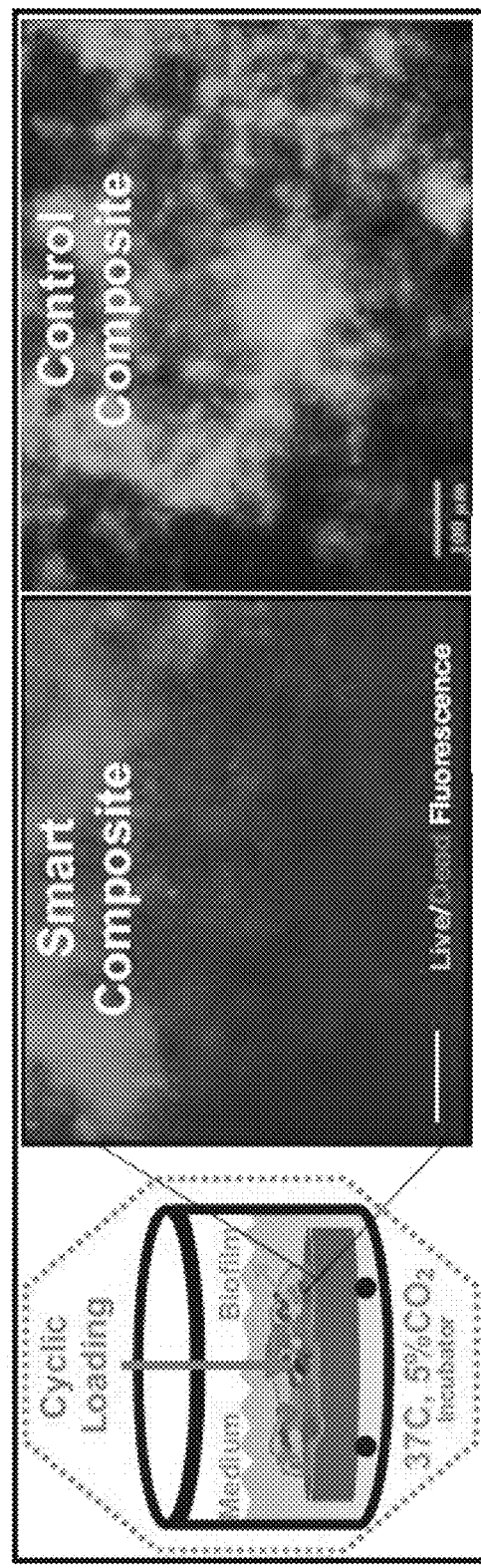
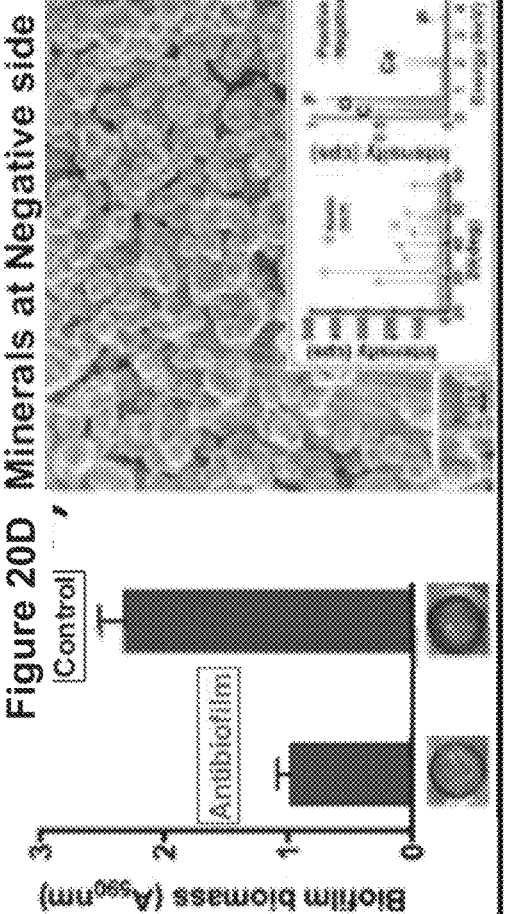
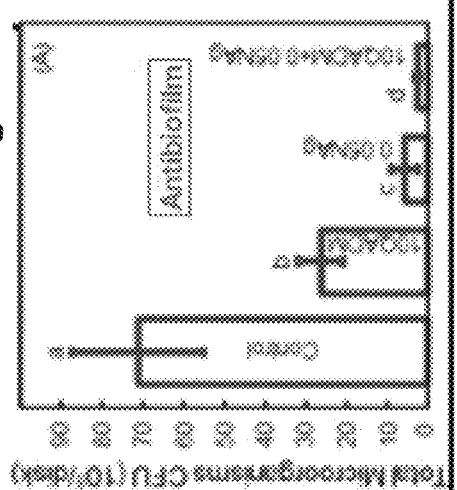
Figure 20A
Figure 20B
Figure 20C
Figure 20D Minerals at Negative side

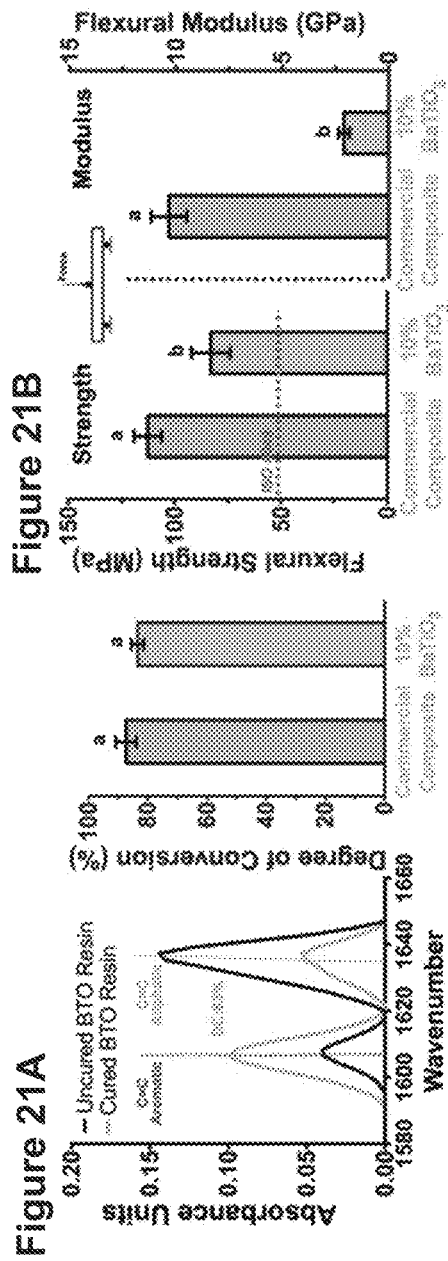

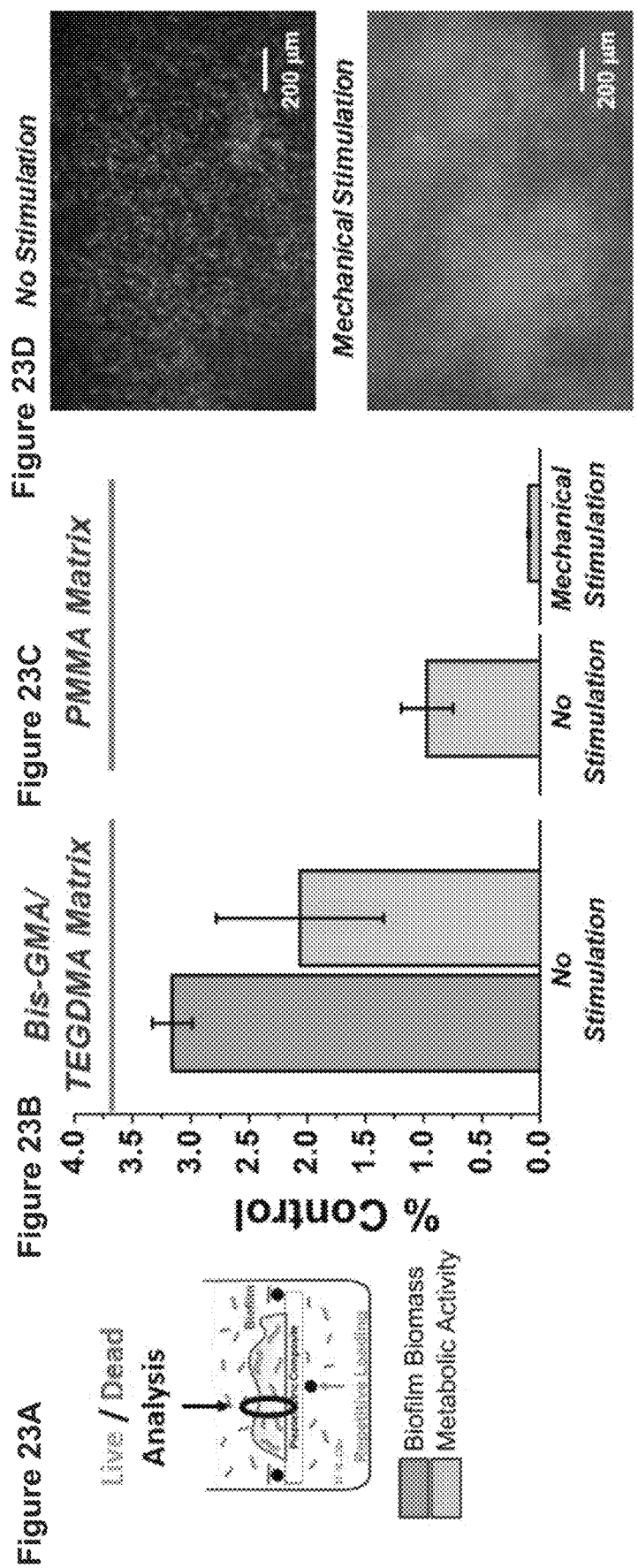

SMART COMPOSITE WITH ANTIBIOFILM, MINERALIZING, AND ANTIINFECTION THERAPEUTIC EFFECTS

CROSS-REFERENCE TO RELATED APPLICATIONS

This application is a national phase application under 35 U.S.C. § 371 claiming benefit to PCT International Application PCT/US2020/024951, filed Mar. 26, 2020, which claims priority under 35 U.S.C. § 119(e) to U.S. Provisional Patent Application Ser. No. 62/823,833, filed Mar. 26, 2019, the disclosures of which are incorporated herein by reference in their entirety.

BACKGROUND OF THE INVENTION

Dental caries remains to be a public health issue with growing trends within the aged and the underserved populations. There is a global need to develop new technologies, biomaterials and policies that further prevent tooth decay and improve health. Millions of resin composite restorations are replaced every year due to secondary caries and fracture. Failure is particularly prevalent for Class V restorations where mechanical stresses and biofilm formation are highest. The bond strength is decreased by the combined weakening effects of chemical attacks from bacteria and mechanical stresses from mastication.

Replacement of failed restorations accounts for nearly 70% of all clinical dental work due to the short clinical service life of resin composites (<7 years). The associated cost with restorative materials and clinics operation is immense. Improvements in the clinical service of restorative materials would offer significant health care benefits to the general public, especially in the aged and the underserved populations.

Thus, there is a need in the art for compositions and methods which reduce the failure rate of composite restorations, and which reduce the costs associated with those failures, and prevent unnecessary loss of additional tooth structure. The present invention satisfies this need.

SUMMARY OF THE INVENTION

The present invention provides a composite comprising a resin matrix and a nanoparticle comprising a piezoelectric material, wherein the nanoparticles are dispersed within the resin matrix. In one embodiment, the piezoelectric material is $BaTiO_3$ (BTO). In one embodiment, the ratio of the nanoparticle to resin matrix is about 1:10 to about 7:10. In another embodiment, the ratio of the nanoparticle to resin matrix is about 1:10, about 4:10 or about 7:10.

In one embodiment, the composite is a dental composite.

In one aspect, the present invention also provides a method of simultaneously treating biofilms and promoting mineralization, the method comprising applying a composite to a tooth, wherein the composite comprising a resin matrix and a nanoparticle comprising a piezoelectric material, wherein the nanoparticles are dispersed within the resin matrix.

In another aspect, the present invention provides a method of simultaneously treating biofilms and promoting antifungal effect, the method comprising applying a composite to a tooth, wherein the composite comprising a resin matrix and a nanoparticle comprising a piezoelectric material, wherein the nanoparticles are dispersed within the resin matrix.

In some embodiments, the mastication forces generate electrical charges at the material's surface, wherein the electrical charges simultaneously repel biofilms and precipitate new minerals. In some embodiments, the mastication forces excite the material, which generates electrical charges at the material's surface, wherein the electrical charges simultaneously repel biofilms and precipitate new minerals.

In yet another aspect, the present invention provides a biomaterial comprising a nanoparticle comprising a piezoelectric material, wherein the piezoelectric material promotes bone growth and prevents or reduces an infection. In one embodiment, the biomaterial is a surface coating of a titanium implant.

In one embodiment, the infection is a bacterial infection. In another embodiment, the infection is a fungal infection.

BRIEF DESCRIPTION OF THE DRAWINGS

The following detailed description of various embodiments of the invention will be better understood when read in conjunction with the appended drawings. For the purpose of illustrating the invention, these are shown in the drawings illustrative embodiments. It should be understood, however, that the invention is not limited to the precise arrangements and instrumentalities of the embodiments shown in the drawings.

FIG. 3 depicts a schematic representation of biomaterial's evolution.

FIG. 18, comprising FIG. 18A through FIG. 18C, depicts a representative example of smart bifunctional biomaterial. FIG. 18A depicts a representative preparation of smart bifunctional biomaterial. FIG. 18B depicts representative obtained samples, representative molded beam and composite microstructure showing filler (blue arrows) distribution at fracture surface. FIG. 18C depicts a representative example of microstructure analysis of smart bifunctional biomaterial and representative results for the evaluation of BTO chemical (EDS) of the fracture surface of the composite, showing that the fillers are indeed BTO. Peaks of Ba and Ti show the nano filler composition.

FIG. 19, comprising FIG. 19A depicts a representative electrical charge generation of the novel composite. FIG. 19B depicts representative piezoelectric coefficient ($d_{33}$) responses of the novel composite.

FIG. 20, comprising FIG. 20A through FIG. 20D, depicts representative examples of anti-biofilm and remineralization evaluations. FIG. 20A depicts a representative example of live/dead fluorescence (Melo M A et al., 2016, ACS applied materials & interfaces, 8:11779-11787). FIG. 20B depicts a representative example of CFU counts (Zhang K et al., 2012, Dental Materials, 28:842-852). FIG. 20C depicts a representative example of biofilm mass (Tawakoli P et al., 2013, Clinical oral investigations, 17:841-850). FIG. 20D depicts a representative example of mineralization on material piezoelectric surface.

FIG. 21, comprising FIG. 21A through FIG. 21B, depicts representative example of development of the piezoelectric composites filled with 10% $BaTiO_3$. Means with different letters are significantly different (p<0.05). The error bars were obtained from N=7 samples for each evaluation. FIG. 21A depicts representative degree of conversion (right) of composites from FTIR spectra (left). FIG. 21B depicts representative mechanical properties including strength (left) and elastic modulus (right).

FIG. 22, comprising FIG. 22A depicts representative model to grow biofilms on samples subjected to simultaneous liquid bacteria and repetitive mechanical loading. FIG. 22B depicts representative S. Mutans biofilm-biomaterial evaluations of commercial and piezoelectric composites with and without repetitive loading.

FIG. 22C depicts representative S. sanguinis biofilm-biomaterial evaluation of piezoelectric composites with repetitive loading.

FIG. 23, comprising FIG. 23A through FIG. 23D, depicts representative antifungal properties of piezoelectric PMMA composites with 10% BTO. Samples (N=5) for each evaluation. FIG. 23A depicts representative model to grow Candida albicans biofilms on samples subjected to simultaneous liquid fungi and repetitive mechanical loading. FIG. 23B depicts representative C. albicans biofilm-biomaterial evaluations of commercial BisGMA resins. FIG. 23C depicts representative commercial PMMA acrylics and new PMMA piezoelectric composites with and without repetitive loading (mechanical stimulation). FIG. 23D depicts representative fluorescent microscopy showing dead (red) and live (green) cells.

FIG. 24, comprising FIG. 24A depicts a schematic representation of a model to form minerals on samples. FIG. 24B depicts representative SEM micrograph of minerals on negative surface. FIG. 24C depicts representative results of chemical analysis of minerals. FIG. 24D depicts representative amount of formed minerals (N=5).

FIG. 26 depicts representative metabolic activity of S. mutans biofilms on composites with different amount of BTO fillers.

DETAILED DESCRIPTION

Figure 1:
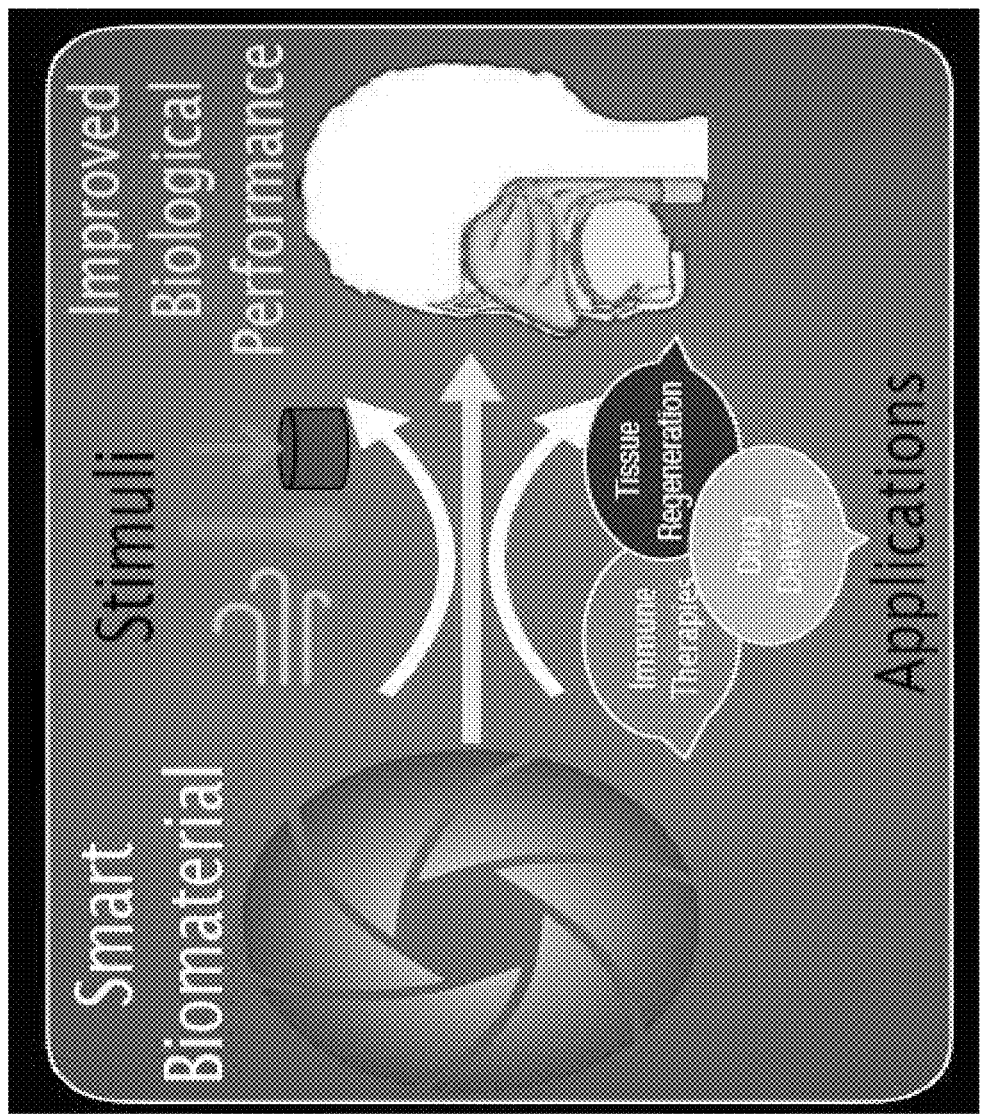
FIG. 1 depicts a schematic representation of smart dental biomaterials for oral health.

The present invention is based, in part, on the development of a novel biocomposite having multi-functions of repeling biofilms, promoting formation of minerals, and having anti-infection properties. In one aspect, the biocomposite comprises a resin matrix and a nanoparticle comprising a piezoelectric material. In one embodiment, the piezoelectric material is $BaTiO_3$ (BTO). In one embodiment, the biocomposite comprises a biomaterial and a nanoparticle comprising a piezoelectric material. In one embodiment, the biocomposite is antibacterial biomaterial, antifungal biomaterial, or any combination thereof. In one embodiment, the composite is used in medical applications (e.g., dentistry, orthopedics, medical devices, basic research, wound healing, dental composites, implant, titanium implant, coatings, such as surface coating of a titanium implant, etc.).

In one embodiment, the invention provides a method for simultaneously treating biofilms, promoting mineralization, treating infection, or any combination thereof. In one embodiment, the method comprising applying a biocomposite to a subject in need thereof. In one embodiment, the biocomposite is applied to a tooth. In one embodiment, mastication forces generate electrical charges at the material's surface, wherein the electrical charges simultaneously repel biofilms and precipitate new minerals. In some embodiments, the mastication forces excite the material, which generates electrical charges at the material's surface, wherein the electrical charges simultaneously repel biofilms and precipitate new minerals.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the term "analog," "analogue," or "derivative" is meant to refer to a chemical compound or molecule made from a parent compound or molecule by one or more chemical reactions. As such, an analog can be a structure having a structure similar to that of the small molecule therapeutic agents described herein or can be based on a scaffold of a small molecule therapeutic agents described herein, but differing from it in respect to certain components or structural makeup, which may have a similar or opposite action metabolically. An analog or derivative can also be a small molecule that differs in structure from the reference molecule, but retains the essential properties of the reference molecule. An analog or derivative may change its interaction with certain other molecules relative to the reference molecule. An analog or derivative molecule may also include a salt, an adduct, tautomer, isomer, or other variant of the reference molecule.

The term "tautomers" are constitutional isomers of organic compounds that readily interconvert by a chemical process (tautomerization).

The term "isomers" or "stereoisomers" refer to compounds, which have identical chemical constitution, but differ with regard to the arrangement of the atoms or groups in space.

As used herein, the term "polymer" refers to a molecule composed of repeating structural units typically connected by covalent chemical bonds. The term "polymer" is also meant to include the terms copolymer and oligomers. In one embodiment, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "nanoparticle" refers to particles having a particle size on the nanometer scale, less than 1 micrometer. For example, the nanoparticle may have a particle size up to about 50 nm. In another example, the nanoparticle may have a particle size up to about 10 nm. In another example, the nanoparticle may have a particle size up to about 6 nm. As used herein, "nanoparticle" refers to a number of nanoparticles, including, but not limited to, nanoclusters, nanocapsules, core-shell nanocapsules, nanovesicles, micelles, block copolymer micelles, lamaellae shaped particles, polymersomes, dendrimers, and other nano-size particles of various other small fabrications that are known to those of skill in the art. The shapes and compositions of nanoparticles may be guided during condensation of atoms by selectively favoring growth of particular crystal facets to produce spheres, rods, wires, discs, cages, core-shell structures and many other shapes. The definitions and understandings of the entities falling within the scope of nanocapsule are known to those of skill in the art, and such definitions are incorporated herein by reference and for the purposes of understanding the general nature of the subject matter of the present application. However, the following discussion is useful as a further understanding of some of these terms.

For example, the term "nanocapsule" refers to a vesicular system or hollow particle with a shell surrounding a core-forming space, which, in certain instances, can be used for transporting a payload on a nanoscale level. A nanocapsule may also be a nano-sized version of a container. The payload of the nanocapsule can be, but is not limited to drugs, medicaments, pharmaceutical compositions, chemical compositions, therapeutic compositions, biological macromolecules, dyes, biological material, immunological compositions, nutritional compositions, vitamins, proteins, nucleic acids, antibodies and vaccines. Various materials may be used for producing such nanocapsules. Nanocapsule refers to a particle having a hollow core that is surrounded by a shell, such that the particle has a size of less than about 1000 nanometers. When a nanocapsule includes a bioactive component, the bioactive component is located in the core that is surrounded by the shell of the nanocapsule.

As used herein, the term "nanocage" refers to a nanocapsule, whereby the shell is not solid, as described for the nanocapsule, but has multiple holes or pores in its shell, thereby making it possible for the payload within the core of the nanocage to come into contact with the surrounding environment. These holes or pores may be regular or irregular in shape and/or spacing on the surface of the particle.

The term "micelle", a useful article in the employment of a general aspect of the present invention, can generally be thought of as a small—on the order of usually nanometers in diameter—aggregate of amphiphilic linear molecules having a polar, or hydrophilic end and an opposite non-polar, or hydrophobic end. These linear molecules can be comprised of simple molecules, or polymeric chains. A micelle can also be referred to as an aggregate of surfactant molecules dispersed in a liquid colloid. A typical micelle in aqueous solution can form an aggregate with the hydrophilic "head" regions in contact with surrounding solvent, and the sequestering of the hydrophobic tail regions in the micelle center. Other and similar definitions, descriptions and understandings of micelles are also known to those of skill in the art and are incorporated herein by reference.

The term "polymersome" as used herein refers to a vesicle-type which is typically composed of block copolymer amphiphiles, i.e., synthetic amphiphiles that have an amphiphilicity similar to that of lipids. By virtue of their amphiphilic nature (having a more hydrophilic block (head) and a more hydrophobic block (tail)), the block copolymers are capable of self-assembling into a head-to-tail and tail-to-head bilayer structure similar to liposomes. Compared to liposomes, polymersomes have much larger molecular weights, with number average molecular weights typically ranging from 1000 to 100000, preferably of from 2500 to 50000 and more preferably from 5000 to 25000, are typically chemically more stable, less leaky, less prone to interfere with biological membranes, and less dynamic due to a lower critical aggregation concentration. These properties result in less opsonisation and longer circulation times. The terms "more hydrophilic" and "more hydrophobic" as used in the context of the ampohiphilic nature of the block copolymers are used in a relative sense. i.e., both can be either hydrophilic or hydrophobic, as long as the difference in polarity between the blocks is sufficient for the formation of polymersomes according to the present invention. In view of the creation of a cavity in which water may be incorporated, it is preferred for the more hydrophilic end of the polymer to be hydrophilic per se. Further, in view of the use as a therapeutic agent carrier, it is desired that also hydrophobic and/or hydrophilic therapeutic agents can be incorporated into the polymersomes. In one embodiment, the hydrophobic end of the polymer is hydrophobic per se. The amphiphilic nature of the block copolymers is preferably realized in the form of a block copolymer comprising a block made up of more hydrophilic monomeric units (A) and a block made up of more hydrophobic units (B), the block copolymer having the general structure $A_nB_m$, with n and m being integers of from 5 to 5000, 10 to 1000, or 10 to 500. It is also conceivable that one or more further units or blocks are built-in, e.g., a unit C with an intermediate hydrophilicity so as to yield a terpolymer having the general structure AnCpBm, with n and m being as defined above, and p being an integer of from 5 to 5000, preferably 10 to 1000, more preferably 10 to 500. Any of the blocks can itself be a copolymer, i.e., comprise different monomeric units of the required hydrophilic respectively hydrophobic nature. In one embodiment, the blocks themselves are homopolymeric. Any of the blocks, in particular the more hydrophilic block, may bear charges. The number and type of charges may depend on the pH of the environment. Any combination of positive and/or negative charges on any of the blocks is contemplated by the present invention.

"Dendrimers" have descriptions, definitions and understandings in the literature. For example, and without limitation and including other and similar definitions, descriptions and understandings in the art, the term dendrimer from the Greek word, "dendron", for tree, can refer to a synthetic, three-dimensional molecule with branching parts. Descriptions and understandings of dendrimers can be gleaned from Holister et al., Dendrimers, Technology White Papers nr. 6, pub. October 2003 by cientifica, as well as the other literature published by those skilled in the art on dendrimers, all of which are incorporated herein by reference.

"Lamella" is a term whose definitions, descriptions and understandings are also known to those of skill in the art and which are incorporated herein by reference. In a very general sense, lamella or lamellae refers to plate-like, gill-shaped or other layered structures.

The definitions, descriptions and understandings of "nanovesicle" are well known to those of skill in the art, and are incorporated herein by reference. For example, "nanovesicle" can refer to a variety of small sac, sac-like or globular structures capable of containing fluid or other material therein The terms "patient," "subject," "individual," and the like are used interchangeably herein, and refer to any animal, or cells thereof whether in vitro or in situ, amenable to the methods described herein. In some non-limiting embodiments, the patient, subject or individual is a human. In various embodiments, the subject is a human subject, and may be of any race, sex, and age.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of at least one sign or symptom of the disease or disorder, the frequency with which such a sign or symptom is experienced by a patient, or both, is reduced.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, such as, a human.

The term "inhibit," as used herein, means to suppress or block an activity or function by at least about ten percent relative to a control value. In various embodiments, the activity is suppressed or blocked by at least 50% compared to a comparator value, or by at least 55%, or by at least 60%, or by at least 65%, or by at least 70%, or by at least 75%, or by at least 80%, or by at least 85%, or by at least 90%, or by at least 95%.

As used herein, the term "diagnosis" refers to the determination of the presence of a disease or disorder. In various embodiments of the present invention, methods for making a diagnosis are provided which permit determination of the presence of a particular disease or disorder.

To "treat" a disease as the term is used herein, means to reduce the frequency and/or severity of at least one sign or symptom of a disease or disorder experienced by a subject.

The terms "effective amount" and "pharmaceutically effective amount" refer to a sufficient amount of an agent to provide the desired biological result. That result can be reduction and/or alleviation of a sign, symptom, or cause of a disease or disorder, or any other desired alteration of a biological system. An appropriate effective amount in any individual case may be determined by one of ordinary skill in the art using routine experimentation.

The term "therapeutic" as used herein means a treatment and/or prophylaxis. A therapeutic effect is obtained by suppression, diminution, remission, prevention, or eradication of at least one sign or symptom of a disease or disorder.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

"Pharmaceutically acceptable" refers to those properties and/or substances which are acceptable to the patient from a pharmacological/toxicological point of view and to the manufacturing pharmaceutical chemist from a physical/ chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

The term "pharmaceutically acceptable salt" refers to any pharmaceutically acceptable salt, which upon administration to the subject is capable of providing (directly or indirectly) a compound as described herein. Such salts preferably are acid addition salts with physiologically acceptable organic or inorganic acids. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methane sulphonate, and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine, and basic amino acids salts. However, it will be appreciated that non-pharmaceutically acceptable salts also fall within the scope of the invention since those may be useful in the preparation of pharmaceutically acceptable salts. Procedures for salt formation are conventional in the art.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

The term "solvate" in accordance with this invention should be understood as meaning any form of the active compound in accordance with the invention in which said compound is bonded by a non-covalent bond to another molecule (normally a polar solvent), including especially hydrates and alcoholates.

As used herein, the term "pharmaceutical composition" refers to a mixture of at least one compound of the invention with other chemical components and entities, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

As used herein, the terms "therapeutic compound", "therapeutic agent", "drug", "active pharmaceutical", and "active pharmaceutical ingredient" are used interchangeably to refer to chemical entities that display certain pharmacological effects in a body and are administered for such purpose. Non-limiting examples of therapeutic agents include, but are not limited to, hydrophilic therapeutic agents, hydrophobic therapeutic agents, antibiotics, antibodies, small molecules, anti-cancer agents, chemotherapeutic agents, immunomodulatory agents, RNA molecules, siRNA molecules, DNA molecules, gene editing agents, gene-silencing agents, CRISPR-associated agents (e.g., guide RNA molecules, endonucleases, and variants thereof), analgesics, vaccines, anticonvulsants; anti-diabetic agents, antifungal agents, antineoplastic agents, anti-parkinsonian agents, anti-rheumatic agents, appetite suppressants, biological response modifiers, cardiovascular agents, central nervous system stimulants, contraceptive agents, dietary supplements, vitamins, minerals, lipids, saccharides, metals, amino acids (and precursors), nucleic acids and precursors, contrast agents, diagnostic agents, dopamine receptor agonists, erectile dysfunction agents, fertility agents, gastrointestinal agents, hormones, immunomodulators, antihypercalcemia agents, mast cell stabilizers, muscle relaxants, nutritional agents, ophthalmic agents, osteoporosis agents, psychotherapeutic agents, parasympathomimetic agents, parasympatholytic agents, respiratory agents, sedative hypnotic agents, skin and mucous membrane agents, smoking cessation agents, steroids, sympatholytic agents, urinary tract agents, uterine relaxants, vaginal agents, vasodilator, anti-hypertensive, hyperthyroids, anti-hyperthyroids, anti-asthmatics and vertigo agents. In certain embodiments, the one or more therapeutic agents are water-soluble, poorly water-soluble drug or a drug with a low, medium or high melting point. The therapeutic agents may be provided with or without a stabilizing salt or salts.

Some examples of active ingredients suitable for use in the pharmaceutical formulations and methods of the present invention include: hydrophilic, lipophilic, amphiphilic or hydrophobic, and that can be solubilized, dispersed, or partially solubilized and dispersed, on or about the nanocluster. The active agent-nanocluster combination may be coated further to encapsulate the agent-nanocluster combination and may be directed to a target by functionalizing the nanocluster with, e.g., aptamers and/or antibodies. Alternatively, an active ingredient may also be provided separately from the solid pharmaceutical composition, such as for co-administration. Such active ingredients can be any compound or mixture of compounds having therapeutic or other value when administered to an animal, particularly to a mammal, such as drugs, nutrients, cosmeceuticals, nutraceuticals, diagnostic agents, nutritional agents, and the like. The active agents described herein may be found in their native state, however, they will generally be provided in the form of a salt. The active agents described herein include their isomers, analogs and derivatives.

The term "antibody", as used herein, refers to an immunoglobulin molecule which is able to specifically bind to a specific epitope of an antigen. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, multiple chain antibodies, intact immunoglobulins, synthetic antibodies, recombinant antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen.

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

A "chimeric antibody" refers to a type of engineered antibody which contains a naturally-occurring variable region (light chain and heavy chains) derived from a donor antibody in association with light and heavy chain constant regions derived from an acceptor antibody.

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

By the term "recombinant antibody" as used herein, is meant an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

An "antibody heavy chain," as used herein, refers to the larger of the two types of polypeptide chains present in antibody molecules in their naturally occurring conformations, and which normally determines the class to which the antibody belongs.

An "antibody light chain," as used herein, refers to the smaller of the two types of polypeptide chains present in antibody molecules in their naturally occurring conformations. Kappa (κ) and lambda (λ) light chains refer to the two major antibody light chain isotypes.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based, in part, on the development of a novel biocomposite having dual functions of repeling biofilms and promoting formation of minerals. In one aspect, the biocomposite comprises a resin matrix and a nanoparticle comprising a piezoelectric material. In one embodiment, the piezoelectric material is $BaTiO_3$ (BTO). In one embodiment, the biocomposite comprises a biomaterial and a nanoparticle comprising a piezoelectric material. In one embodiment, the biomaterial is a surface coating of a titanium implant.

In one embodiment, the invention provides a method for simultaneously treating biofilms and promoting mineralization. In one embodiment, the method comprising applying a biocomposite to a subject in need thereof. In one embodiment, the biocomposite is applied to a tooth. In one embodiment, mastication forces generate electrical charges at the material's surface, wherein the electrical charges simultaneously repel biofilms and precipitate new minerals. In some embodiments, the mastication forces excite the material, which generates electrical charges at the material's surface, wherein the electrical charges simultaneously repel biofilms and precipitate new minerals.

The present invention also relates, in part, to the use of piezoelectric biomaterials as antibacterial and antifungal biomaterial/mechanism. The piezoelectric biomaterial can be provided in a variety of configurations (embedded in resin composites, as surface treatment of existing biomaterials) for use in several medical applications including dentistry, orthopedics, medical devices, basic research, wound healing.

Composites/Biomaterials

In one aspect, the present invention provides a composite comprising a resin matrix and one or more nanoparticles. In one embodiment, the composite is a multi-functional composite. In some embodiments, the composite possesses anti-biofilm functionality, anti-infection functionality (e.g., anti-bacterial functionality, anti-fungal functionality, anti-viral functionality, etc.), anti-inflammatory functionality, mineralizing functionality, or any combination thereof. Thus, in some embodiments, the composite comprises an anti-biofilm composite, anti-infection composite (e.g., anti-bacterial composite, anti-fungal composite, anti-viral composite, etc.), anti-inflammatory composite, mineralizing composite, or any combination thereof.

In one embodiment, the composite comprises a resin matrix. In one embodiment, the composite comprises a polymer, resin, cement, bonding agent, filler, or any combination thereof. In one embodiment, the polymer may be a straight chain polymer (i.e., linear polymer) or a branched chain polymer (i.e., branched polymer), including hyper-branched polymers. In one embodiment the polymer is a branched polymer. In one embodiment, the polymer is cross-linked.

In some embodiments, the polymer comprises a homopolymer, copolymer, block copolymer, or any combination thereof. In some embodiments, the block copolymer is a triblock, tetrablock, pentablock, or at least six block copolymer.

In one embodiment, the polymer has molecular weight of 5 kDa-3000 kDa. For example, in one embodiment, the polymer has a molecular weight of 5 kDa-2000 kDa, 5 kDa-1500 kDa, 5 kDa-1000 kDa, 5 kDa-800 kDa, 5 kDa-500 kDa, 5 kDa-300 kDa or 5 kDa-200 kDa or 800 kDa-3000 kDa.

In some embodiments, the polymer is a polyacrylate, polymethacrylate, polyamine, polyalkyleneimine (e.g., polyethyleneimine), polyallylamine, polyamidoamine, polyolefin, poly(amino-co-ester), or any combination thereof. Examples of polymers include, but are not limited to, polymethyl methacrylate (PMMA), poly bisphenol A diglycidyl dimethacrylate, poly triethylene glycol dimethacrylate, polyethyleneimine (PEI), chitosan, poly(2-N,N-dimethyl-aminoethylmethacrylate), poly-L-lysine, poly(ethylene oxide) (PEO) block copolymer, poly(ethylethylene) (PEE), poly(butadiene) (PB or PBD), poly(styrene) (PS), poly(isoprene) (PI), poly(lactide-co-glycolic acid) (PLGA), biodegradable PLGA, polyethylene glycol (PEG), poly(lactide-co-glycolic acid)-polyethylene glycol (PLGA-PEG), poly(lactide-co-glycolic acid)-block-polyethylene glycol (PLGA-b-PEG), biodegradable PLGA-PEG, biodegradable PLGA-b-PEG, polyanhydride, polyanhydride-block-PEG copolymers, zwitterionic poly(carbobetaine), zwitterionic poly(sulfobetaine)-containing, zwitterionic poly(carbobetaine) and zwitterionic poly(sulfobetaine)-containing copolymers, poly(acrylic acid-co-distearin acrylate), poly(trimethylene carbonate)-block-poly(L-gluatamic acid), poly(ethylene glycol-block-L-aspartic acid), poly(2-hydroxyethyl-co-octadecyl aspartamide), poly(ethylene glycol-co-trimethylene carbonate-co-caprolactone, polypropylene oxide block copolymers, polyethylene oxide-block-polypropylene oxide copolymers, poly(ε-caprolactone) (PCL) diblock co-polymer, poly(ethylene oxide)-block-poly(ε-caprolactone) (PEO-b-PCL) based diblock copolymers, poly(lactic acid), poly(glycolide), poly(lactic-coglycolic acid), poly(3-hydroxybutyrate), or any combination thereof.

In some embodiments, the composite comprises bonding agents/linking molecules. Examples of linking molecules include, but are not limited to, bisphenol A diglycidyl dimethacrylate, triethylene glycol dimethacrylate, camphorquinone, ethyl 4-dimethylaminobenzoate, poly(ethylene glycol) and its derivatives, azide compounds, maleimide compounds, hydzrazine compounds, dibenzo-cyclooctyne (DBCO) compounds, dithiol compounds, dithiol compounds with hydrazide and/or carboxylic functionality, or single thiols and/or amines or their derivatives.

In one embodiment, the composite comprises at least one filler. In various embodiments, the filler is a nanoparticle. In one embodiment, the nanoparticle is any type of nanoparticle, including, but not limited to, nanocapsules, nanocarrier, nanoclusters, nanovesicles, micelles, block copolymer micelles, lamellae shaped particles, polymersomes, dendrimers, polymer vesicle, and nano-size particles of various other small fabrications that are known to those in the art.

In one embodiment, the nanoparticle is a ceramic nanoparticle. In one embodiment, the nanoparticles comprise a piezoelectric material. For example, in one embodiment, the piezoelectric material is $BaTiO_3$ (BTO).

In one embodiment, the nanoparticles are dispersed within the resin matrix. In one embodiment, the ratio of the nanoparticle to resin matrix is about 1:100 to about 100:1. In one embodiment, the ratio of the nanoparticle to resin matrix is about 1:100 to about 1:1. In one embodiment, the ratio of the nanoparticle to resin matrix is about 1:10 to about 9:10. In one embodiment, the ratio of the nanoparticle to resin matrix is about 1:10 to about 8:10. In one embodiment, the ratio of the nanoparticle to resin matrix is about 1:10 to about 7:10. In one embodiment, the ratio of the nanoparticle to resin matrix is about 1:10 to about 6:10. In one embodiment, the ratio of the nanoparticle to resin matrix is about 1:10 to about 5:10. In one embodiment, the ratio of the nanoparticle to resin matrix is about 1:10 to about 4:10. In one embodiment, the ratio of the nanoparticle to resin matrix is about 1:10 to about 3:10. In one embodiment, the ratio of the nanoparticle to resin matrix is about 1:10 to about 2:10.

In one embodiment, the ratio of the nanoparticle to resin matrix is about 1:100. In one embodiment, the ratio of the nanoparticle to resin matrix is about 1:10. In one embodiment, the ratio of the nanoparticle to resin matrix is about 2:10. In one embodiment, the ratio of the nanoparticle to resin matrix is about 3:10. In one embodiment, the ratio of the nanoparticle to resin matrix is about 4:10. In one embodiment, the ratio of the nanoparticle to resin matrix is about 5:10. In one embodiment, the ratio of the nanoparticle to resin matrix is about 6:10. In one embodiment, the ratio of the nanoparticle to resin matrix is about 7:10. In one embodiment, the ratio of the nanoparticle to resin matrix is about 8:10. In one embodiment, the ratio of the nanoparticle to resin matrix is about 9:10. In one embodiment, the ratio of the nanoparticle to resin matrix is about 1:1. In one embodiment, the ratio of the nanoparticle to resin matrix is about 100:1.

In one aspect of the invention, the composite further comprises one or more therapeutic agents. In one embodiment, the nanoparticle comprises the therapeutic agent. In one embodiment, the therapeutic agent is a hydrophobic therapeutic agent. In one embodiment, the therapeutic agent is a hydrophilic therapeutic agent. Examples of such therapeutic agents include, but are not limited to, one or more drugs, proteins, amino acids, peptides, antibodies, antibiotics, anti-inflammatory agents, anti-infection agents, antibacterial agents, anti-viral agents, anti-fungal agents, small molecules, anti-cancer agents, chemotherapeutic agents, immunomodulatory agents, RNA molecules, siRNA molecules, DNA molecules, gene editing agents, gene-silencing agents, CRISPR-associated agents (e.g., guide RNA molecules, endonucleases, and variants thereof), medical imaging agents, therapeutic moieties, one or more non-therapeutic moieties or a combination to target cancer or atherosclerosis, selected from folic acid, peptides, proteins, aptamers, antibodies, siRNA, poorly water soluble drugs, anti-cancer drugs, antibiotics, analgesics, vaccines, anticonvulsants; anti-diabetic agents, antifungal agents, antineoplastic agents, anti-parkinsonian agents, anti-rheumatic agents, appetite suppressants, biological response modifiers, cardiovascular agents, central nervous system stimulants, contraceptive agents, dietary supplements, vitamins, minerals, lipids, saccharides, metals, amino acids (and precursors), nucleic acids and precursors, contrast agents, diagnostic agents, dopamine receptor agonists, erectile dysfunction agents, fertility agents, gastrointestinal agents, hormones, immunomodulators, antihypercalcemia agents, mast cell stabilizers, muscle relaxants, nutritional agents, ophthalmic agents, osteoporosis agents, psychotherapeutic agents, parasympathomimetic agents, parasympatholytic agents, respiratory agents, sedative hypnotic agents, skin and mucous membrane agents, smoking cessation agents, steroids, sympatholytic agents, urinary tract agents, uterine relaxants, vaginal agents, vasodilator, anti-hypertensive, hyperthyroids, anti-hyperthyroids, anti-asthmatics and vertigo agents, or any combinations thereof.

In one embodiment, the therapeutic agent may be an anti-infection agent. Any suitable anti-infection agent may be used in the compositions and methods of the present disclosure. The selection of a suitable anti-infection agent may depend upon, among other things, the type of infection to be treated and the composite of the present disclosure. In certain embodiments, the anti-infection agent may be an anti-bacterial agent, anti-fungal agent, anti-viral agent, or any combination thereof. Thus, in certain embodiments, the anti-infection agent may be effective for treating one or more of bacterial infection, viral infection, fungal infection, or any combination thereof.

Examples of examples of antibacterial agents or antibiotics include, but are not limited to, aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithromycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

Additional nonlimiting examples of antibacterial agents include Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmnenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Gatifloxacin Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafingin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Suifabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Examples of anti-fungal agent include, but are not limited to, polyenes (e.g., amphotericin b, candicidin, mepartricin, natamycin, and nystatin), allylamines (e.g., butenafine, and naftifine), imidazoles (e.g., bifonazole, butoconazole, chlordantoin, flutrimazole, isoconazole, ketoconazole, and lanoconazole), thiocarbamates (e.g., tolciclate, tolindate, and tolnaftate), triazoles (e.g., fluconazole, itraconazole, saperconazole, and terconazole), bromosalicylchloranilide, buclosamide, calcium propionate, chlorphenesin, ciclopirox, azaserine, griseofulvin, oligomycins, neomycin undecylenate, pyrrolnitrin, siccanin, tubercidin, and viridin. Additional examples of antifungal compounds include but are not limited to Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofingin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafuigin; Undecylenic Acid; Viridoflilvin; Zinc Undecylenate; and Zinoconazole Hydrochloride.

Examples of anti-viral agents include, but are not limited to, proteins, polypeptides, peptides, fusion protein antibodies, nucleic acid molecules, organic molecules, inorganic molecules, and small molecules that inhibit or reduce the attachment of a virus to its receptor, the internalization of a virus into a cell, the replication of a virus, or release of virus from a cell. Many examples of antiviral compounds that can be used in combination with the compounds of the invention are known in the art and include but are not limited to: rifampicin, nucleoside reverse transcriptase inhibitors (e.g., AZT, ddl, ddC, 3TC, d4T), non-nucleoside reverse transcriptase inhibitors (e.g., Efavirenz, Nevirapine), protease inhibitors (e.g., aprenavir, indinavir, ritonavir, and saquinavir), idoxuridine, cidofovir, acyclovir, ganciclovir, zanamivir, amantadine, and Palivizumab. Other examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscamet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime, zinc, heparin, anionic polymers.

In one embodiment, the therapeutic agent may be an anti-inflammatory agent. Any suitable anti-inflammatory agent may be used in the compositions and methods of the present disclosure. The selection of a suitable anti-inflammatory agent may depend upon, among other things, the type of inflammation to be treated and the composite of the present disclosure. Examples of anti-inflammatory agents include, but are not limited to, non-steroidal anti-inflammatory drugs (NSAIDs), steroidal anti-inflammatory drugs, beta-agonists, anticholingeric agents, antihistamines (e.g., ethanolamines, ethylenediamines, piperazines, and phenothiazine), and methyl xanthines. Examples of NSAIDs include, but are not limited to, aspirin, ibuprofen, salicylates, acetominophen, celecoxib, diclofenac, etodolac, fenoprofen, indomethacin, ketoralac, oxaprozin, nabumentone, sulindac, tolmentin, rofecoxib, naproxen, ketoprofen and nabumetone. Such NSAIDs function by inhibiting a cyclooxgenase enzyme (e.g., COX-1 and/or COX-2). Examples of steroidal anti-inflammatory drugs include, but are not limited to, glucocorticoids, dexamethasone, cortisone, hydrocortisone, prednisone, prednisolone, triamcinolone, azulfidine, and eicosanoids such as prostaglandins, thromboxanes, and leukotrienes.

In one embodiment, the therapeutic agent may be an anti-cancer agent. Any suitable anti-cancer agent may be used in the compositions and methods of the present disclosure. The selection of a suitable anti-cancer agent may depend upon, among other things, the type of cancer to be treated and the composite of the present disclosure. In certain embodiments, the anti-cancer agent may be effective for treating one or more of pancreatic cancer, esophageal cancer, rectal cancer, colon cancer, prostate cancer, kidney cancer, liver cancer, breast cancer, ovarian cancer, and stomach cancer. Examples of anti-cancer agents include, but is not limited to, chemotherapeutic agents, antiproliferative agents, anti-tumor agents, checkpoint inhibitors, and anti-angiogenic agents. For example, in one embodiment, the anti-cancer agent is gemcitabine, doxorubicin, 5-Fu, tyrosine kinase inhibitors, sorafenib, trametinib, rapamycin, fulvestrant, ezalutamide, or paclitaxel.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The inhibitors of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (*vinca* alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan;

cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase;

peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

In some embodiments, the anti-cancer agent may be a prodrug form of an anti-cancer agent. As used herein, the term "prodrug form" and its derivatives is used to refer to a drug that has been chemically modified to add and/or remove one or more substituents in such a manner that, upon introduction of the prodrug form into a subject, such a modification may be reversed by naturally occurring processes, thus reproducing the drug. The use of a prodrug form of an anti-cancer agent in the compositions, among other things, may increase the concentration of the anti-cancer agent in the compositions of the present disclosure. In certain embodiments, an anti-cancer agent may be chemically modified with an alkyl or acyl group or some form of lipid. The selection of such a chemical modification, including the substituent(s) to add and/or remove to create the prodrug, may depend upon a number of factors including, but not limited to, the particular drug and the desired properties of the prodrug. One of ordinary skill in the art, with the benefit of this disclosure, will recognize suitable chemical modifications.

Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, which bind to the specific antigens of interest.

One skilled in the art would appreciate, based upon the disclosure provided herein, that the antibody can specifically bind with any portion of an antigen target, which can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

The antibodies can be produced by immunizing an animal such as, but not limited to, a rabbit, a mouse or a camel, with an antigenic protein of the invention, or a portion thereof, by immunizing an animal using a protein comprising at least a portion of the antigen, or a fusion protein including a tag polypeptide portion comprising, for example, a maltose binding protein tag polypeptide portion, covalently linked with a portion comprising the appropriate amino acid residues. One skilled in the art would appreciate, based upon the disclosure provided herein, that smaller fragments of these proteins can also be used to produce antibodies that specifically bind the antigen of interest.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

Further, the skilled artisan, based upon the disclosure provided herein, would appreciate that using a non-conserved immunogenic portion can produce antibodies specific for the non-conserved region thereby producing antibodies that do not cross-react with other proteins which can share one or more conserved portions. Thus, one skilled in the art would appreciate, based upon the disclosure provided herein, that the non-conserved regions of an antigen of interest can be used to produce antibodies that are specific only for that antigen and do not cross-react non-specifically with other proteins.

The invention encompasses monoclonal, synthetic antibodies, and the like. One skilled in the art would understand, based upon the disclosure provided herein, that the crucial feature of the antibody of the invention is that the antibody bind specifically with an antigen of interest. That is, the antibody of the invention recognizes an antigen of interest or a fragment thereof (e.g., an immunogenic portion or antigenic determinant thereof).

The skilled artisan would appreciate, based upon the disclosure provided herein, that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods, such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

In some embodiments, a non-human antibody is humanized, where specific sequences or regions of the antibody are modified to increase similarity to an antibody naturally produced in a human or fragment thereof. A humanized antibody can be produced using a variety of techniques known in the art, including but not limited to, CDR-grafting (see, e.g., European Patent No. EP 239,400; International Publication No. WO 91/09967; and U.S. Pat. Nos. 5,225, 539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565, 332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

In one embodiment, the antibody fragment provided herein is a single chain variable fragment (scFv). In various embodiments, the antibodies of the invention may exist in a variety of other forms including, for example, Fv, Fab, and (Fab') 2, as well as bi-functional (i.e. bi-specific) hybrid antibodies (e.g., Lanzavecchia et al., Eur. J. Immunol. 17, 105 (1987)). In some embodiments, the antibodies and fragments thereof of the invention bind a cell bearing antigen, TCR, and/or BCR with wild-type or enhanced affinity. In some embodiments, the antibodies and fragments thereof of the invention bind a T cell bearing TCR with wild-type or enhanced affinity. In some embodiments, the antibodies and fragments thereof of the invention bind a B cell bearing BCR with wild-type or enhanced affinity. In various embodiments, a human scFv may also be derived from a yeast display library.

ScFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise flexible polypeptide linker (e.g., a Ser-Gly linker) with an optimized length and/or amino acid composition. The flexible polypeptide linker length can greatly affect how the variable regions of an scFv fold and interact. In fact, if a short polypeptide linker is employed (e.g., between 5-10 amino acids, intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

The scFv can comprise a polypeptide linker sequence of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The flexible polypeptide linker sequence may comprise any naturally occurring amino acid. In some embodiments, the flexible polypeptide linker sequence comprises amino acids glycine and serine. In another embodiment, the flexible polypeptide linker sequence comprises sets of glycine and serine repeats such as (Gly4Ser)n, where n is a positive integer equal to or greater than 1. In one embodiment, the flexible polypeptide linkers include, but are not limited to, (Gly4Ser)4 or (Gly4Ser)3. Variation in the flexible polypeptide linker length may retain or enhance activity, giving rise to superior efficacy in activity studies.

In one embodiment, the therapeutic agent is one or more non-therapeutic moieties. In some embodiments, the composite comprises one or more therapeutic moieties, one or more non-therapeutic moieties, or any combination thereof.

In some embodiments, the composite further comprises at least one stabilizer. In some embodiments, the stabilizer is a primary particle and/or secondary stabilizers, which may be polymers or other small molecules. Non-limiting examples of primary particle and/or secondary stabilizers for use with the present invention include, e.g., starch, modified starch, and starch derivatives, gums, including but not limited to polymers, polypeptides, albumin, amino acids, thiols, amines, carboxylic acid and combinations or derivatives thereof. Other examples include xanthan gum, alginic acid, other alginates, benitoniite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, potassium polymethacrylate, carrageenan (and derivatives), gum karaya and biosynthetic gum. Other examples of useful primary particle and/or secondary stabilizers include polymers such as: polycarbonates (linear polyesters of carbonic acid); microporous materials (bisphenol, a microporous poly(vinylchloride), microporous polyamides, microporous modacrylic copolymers, microporous styrene-acrylic and its copolymers); porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(mides), poly(benzimidazoles), collodion, regenerated proteins, semi-solid cross-linked poly(vinylpyrrolidone).

In some embodiments, the composite may optionally further comprise a biocompatible metal. Examples of biocompatible metals include, but are not limited to, titanium, copper, copper sulfide, iron oxide, cobalt and noble metals, such as gold and/or silver. One of ordinary skill in the art will be able to select of a suitable type of nanoparticle taking into consideration at least the type of imaging and/or therapy to be performed.

In some embodiments, the composite comprises therapeutic agent with controlled release that can be "triggered" by one of the following stimulus: polymer degradation, enzyme sensitive polymers, or by an external stimulus, such as electrical charge, acoustic waves, mastication load, pH change, ultrasound, light, UV light, NIR light. Thus, in some embodiments, the composites of the present disclosure may be "remotely triggered" by applying stimulus (e.g., energy, such as electrical charge, acoustic waves, mastication load) to the composite. In some embodiments, the energy, such as an electrical charge, acoustic waves, mastication load, electromagnetic field, magnetic field, optical methods (e.g., ultraviolet (UV) irradiation, UV-vis-NIR irradiation, infrared (IR) irradiation, NIR irradiation), or specific radiofrequencies, may be applied to the composite thereby causing the release of a therapeutic agent from the nanoparticle further comprising the therapeutic agent. For example, in one embodiment, an electrical charge is applied to a composite comprising a therapeutic agent, wherein the electrical charge causes the release of the therapeutic agent from the composite. In another embodiment, an acoustic wave is applied to a composite comprising a therapeutic agent, wherein the acoustic waves cause the release of the therapeutic agent from the composite. In another embodiment, a mastication load is applied to a composite comprising a therapeutic agent, wherein the mastication load causes the release of the therapeutic agent from the composite. In some embodiments, this may provide a clinician the ability to control and visualize drug therapy noninvasively.

In one aspect of the invention, the composite is a biomaterial. In one embodiment, the biomaterial comprises a nanoparticle comprising a piezoelectric material.

In one embodiment, the biomaterial is a medical device. In one embodiment, the medical device is an implant. In one embodiment, the medical device is a catheter. In one embodiment, the medical device is a dental composite. In one embodiment, the biomaterial is a coating. In one embodiment, the biomaterial is a surface coating. In one embodiment, the biomaterial is a surface coating of medical devices. For example, in one embodiment, the biomaterial is a surface coating of titanium implant.

In one embodiment, the composite promotes bone growth, prevents or reduces an infection, prevents or reduces inflammation, prevents or treats diseases or disorders, or any combination thereof. In some embodiments, the infection is a bacterial infection, fungal infection, viral infection, or any combination thereof. For example, in one embodiment, the piezoelectric material promotes bone growth and prevents or reduces an infection. In another embodiment, the composite improves oral health and prevents oral cancer.

In various aspect, the present invention also provides compositions comprising at least one composite of the present invention.

Method of Treating Biofilms, Promoting Mineralization, Promoting Anti-Infection Effect, and/or Promoting Anti-Inflammatory Effect The present invention also provides a method of treating biofilms, promoting mineralization, promoting anti-infection effect (e.g., promoting anti-bacterial effect, promoting anti-fungal effect, promoting anti-viral effect, etc.), promoting anti-inflammatory effect, preventing or treating diseases or disorders, or any combination thereof in a subject in need thereof. In one aspect, the present invention provides a method of preventing, reducing, or treating infection, preventing, reducing, or treating inflammation, or any combination thereof in a subject in need thereof. In one embodiment, the present invention provides a method of preventing, reducing, or treating fungal infection, bacterial infection, viral infection, or any combination thereof in a subject in need thereof. Thus, in some embodiments, the disease or disorder is an infection, inflammation, cancer, or any combination thereof.

In various aspects, the present invention comprises a method of simultaneously treating biofilms, promoting mineralization, promoting anti-infection effect (e.g., promoting anti-bacterial effect, promoting anti-fungal effect, promoting anti-viral effect, etc.), promoting anti-inflammatory effect, preventing or treating diseases or disorders, preventing, reducing, or treating infection, preventing, reducing, or treating inflammation, and improving health of a subject in need thereof.

In various embodiments, the method comprises administering at least one composite of the present invention to the subject in need thereof. In one embodiment, the method comprises applying at least one composite of the present invention to the subject in need thereof. For example, in one embodiment, the method comprises applying a composite to a tooth of the subject in need thereof.

In various embodiments, the method comprises a stimulus. In various embodiments, the method comprises a triggering stimulus. In various embodiments, the triggering stimulus repel biofilms, promote mineralization, promote anti-infection effect (e.g., anti-bacterial effect, anti-fungal effect, anti-viral effect, etc.), promote anti-inflammatory effect, or any combination thereof. For example, in one embodiment, the method comprises mastication forces. In one embodiment, the mastication forces generate electrical charges at the composite's surface. In some embodiments, the mastication forces excite the material, which generates electrical charges at the material's surface. In some embodiments, the electrical charges repel biofilms, precipitate new minerals, or a combination thereof.

In another aspect, the present invention provides a method of improving health of a subject in need thereof. For example, in one embodiment, the present invention provides a method of improving oral health of a subject in need thereof. Thus, in one embodiment, the present invention provides a method of improving oral health of a subject in need thereof, which prevents oral cancer.

The following are non-limiting examples of cancers that can be prevented or treated by the disclosed methods and composites: acute lymphoblastic; acute myeloid leukemia; adrenocortical carcinoma; adrenocortical carcinoma, childhood; appendix cancer; basal cell carcinoma; bile duct cancer, extrahepatic; bladder cancer; bone cancer; osteosarcoma and malignant fibrous histiocytoma; liposarcoma and anaplastic liposarcoma; brain stem glioma, childhood; brain tumor, adult; brain tumor, brain stem glioma, childhood; brain tumor, central nervous system atypical teratoid/rhabdoid tumor, childhood; central nervous system embryonal tumors; cerebellar astrocytoma; cerebral astrocytotna/malignant glioma; craniopharyngioma; ependymoblastoma; ependymoma; medulloblastoma; medulloepithelioma; pineal parenchymal tumors of intermediate differentiation; supratentorial primitive neuroectodermal tumors and pineoblastoma; visual pathway and hypothalamic glioma; brain and spinal cord tumors; breast cancer; bronchial tumors; Burkitt lymphoma; carcinoid tumor; carcinoid tumor, gastrointestinal; central nervous system atypical teratoid/rhabdoid tumor; central nervous system embryonal tumors; central nervous system lymphoma; cerebellar astrocytoma cerebral astrocytoma/malignant glioma, childhood; cervical cancer; chordoma, childhood; chronic lymphocytic leukemia; chronic myelogenous leukemia; chronic myeloproliferative disorders; colon cancer; colorectal cancer; craniopharyngioma; cutaneous T-cell lymphoma; esophageal cancer; Ewing family of tumors; extragonadal germ cell tumor; extrahepatic bile duct cancer; eye cancer, intraocular melanoma; eye cancer, retinoblastoma; biliary track cancer, cholangiocarcinoma, anal cancer, neuroendocrine tumors, small bowel cancer, gallbladder cancer; gastric (stomach) cancer; gastrointestinal carcinoid tumor; gastrointestinal stromal tumor (gist); germ cell tumor, extracranial; germ cell tumor, extragonadal; germ cell tumor, ovarian; gestational trophoblastic tumor; glioma; glioma, childhood brain stem; glioma, childhood cerebral astrocytoma; glioma, childhood visual pathway and hypothalamic; hairy cell leukemia; head and neck cancer; hepatocellular (liver) cancer; histiocytosis, langerhans cell; Hodgkin lymphoma; hypopharyngeal cancer; hypothalamic and visual pathway glioma; intraocular melanoma; islet cell tumors; kidney (renal cell) cancer; Langerhans cell histiocytosis; laryngeal cancer; leukemia, acute lymphoblastic; leukemia, acute myeloid; leukemia, chronic lymphocytic; leukemia, chronic myelogenous; leukemia, hairy cell; lip and oral cavity cancer; liver cancer; lung cancer, non-small cell; lung cancer, small cell; lymphoma, aids-related; lymphoma, burkitt; lymphoma, cutaneous T-cell; lymphoma, non-Hodgkin lymphoma; lymphoma, primary central nervous system; macroglobulinemia, Waldenstrom; malignant fibrous histiocvtoma of bone and osteosarcoma; medulloblastoma; melanoma; melanoma, intraocular (eye); Merkel cell carcinoma; mesothelioma; metastatic squamous neck cancer with occult primary; mouth cancer; multiple endocrine neoplasia syndrome, (childhood); multiple myeloma/plasma cell neoplasm; mycosis; fungoides; myelodysplastic syndromes; myelodysplastic/myeloproliferative diseases; myelogenous leukemia, chronic; myeloid leukemia, adult acute; myeloid leukemia, childhood acute; myeloma, multiple; myeloproliferative disorders, chronic; nasal cavity and paranasal sinus cancer; nasopharyngeal cancer; neuroblastoma; non-small cell lung cancer; oral cancer; oral cavity cancer; oropharyngeal cancer; osteosarcoma and malignant fibrous histiocytoma of bone; ovarian cancer; ovarian epithelial cancer; ovarian germ cell tumor; ovarian low malignant potential tumor; pancreatic cancer, islet cell tumors; papillomatosis; parathyroid cancer; penile cancer; pharyngeal cancer; pheochromocytoma; pineal parenchymal tumors of intermediate differentiation; pineoblastoma and supratentorial primitive neuroectodermal tumors; pituitary tumor; plasma celt neoplasm/multiple myeloma; pleuropulmonary blastoma; primary central nervous system lymphoma; prostate cancer; rectal cancer; renal cell (kidney) cancer; renal pelvis and ureter, transitional cell cancer; respiratory tract carcinoma involving the nut gene on chromosome 15; retinoblastoma; rhabdomyosarcoma; salivary gland cancer; sarcoma, ewing family of tumors; sarcoma, Kaposi; sarcoma, soft tissue; sarcoma, uterine; Sezary syndrome; skin cancer (nonmelanoma); skin cancer (melanoma); skin carcinoma, Merkel cell; small cell lung cancer; small intestine cancer; soft tissue sarcoma; squamous cell carcinoma, squamous neck cancer with occult primary, metastatic; stomach (gastric) cancer; supratentorial primitive neuroectodermal tumors; T-cell lymphoma, cutaneous; testicular cancer; throat cancer; thymoma and thymic carcinoma; thyroid cancer; transitional cell cancer of the renal pelvis and ureter; trophoblastic tumor, gestational; urethral cancer; uterine cancer, endometrial; uterine sarcoma; vaginal cancer; vulvar cancer; Waldenstrom macroglobulinemia; and Wilms tumor.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Smart Dental Biomaterials for Oral Health

The data presented herein demonstrates novel smart biomaterials which change one or more of their properties in response to external stimuli. These biomaterials can smartly interact with the oral environment to improve overall health (FIG. 1).

Figure 2:
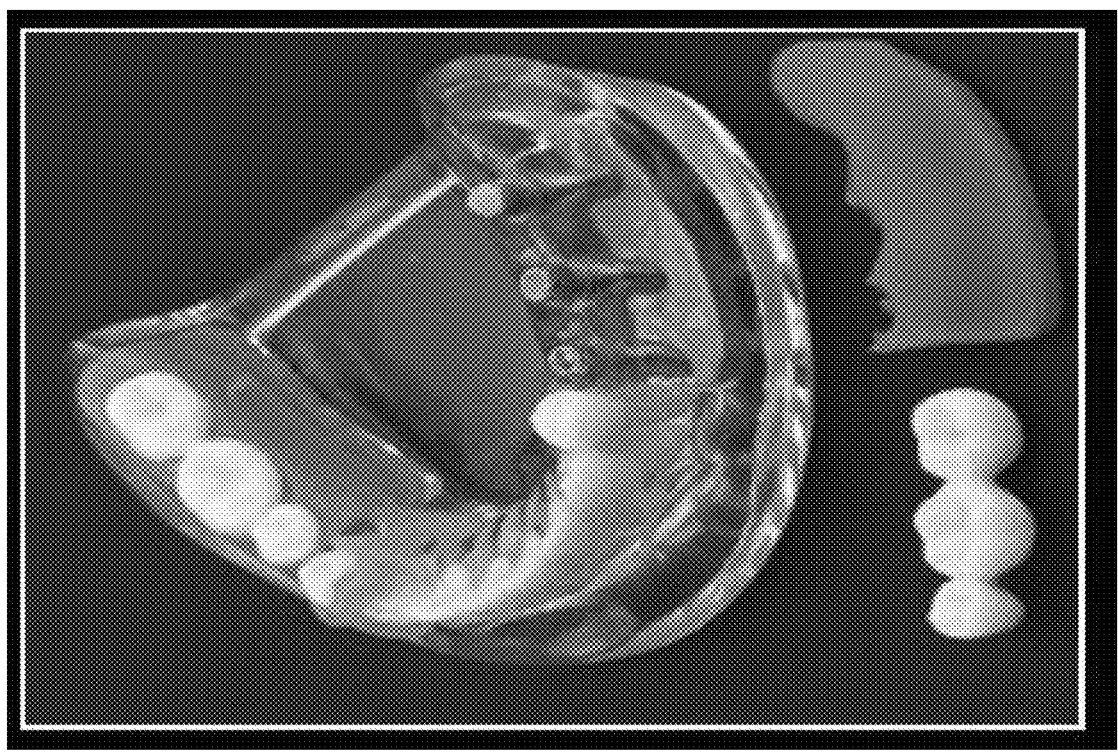
FIG. 2 depicts a representative example of dental biomaterials.
Figure 4:
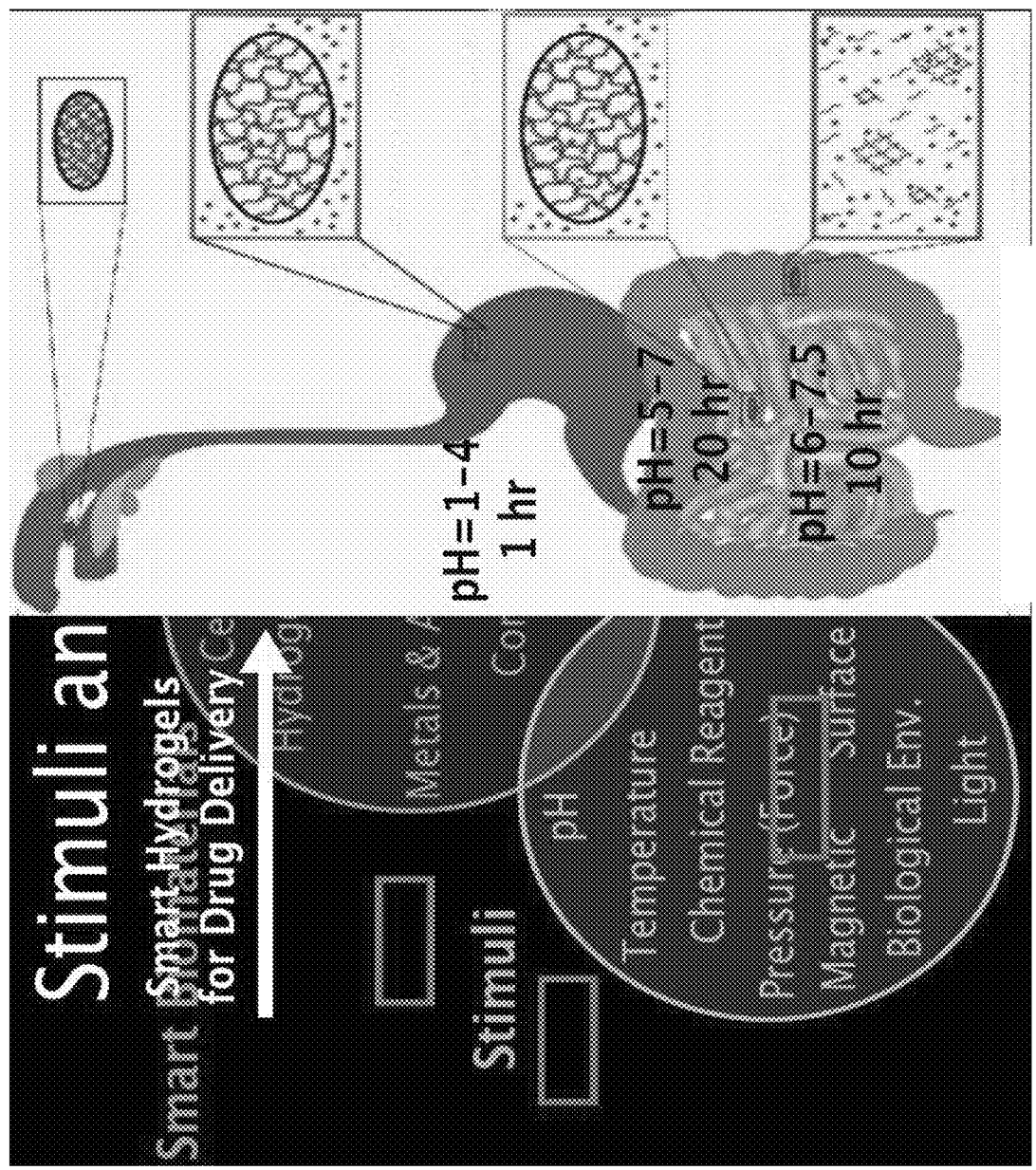
FIG. 4 depicts a schematic representation of functionality examples of smart biomaterials and stimuli.
Figure 5:
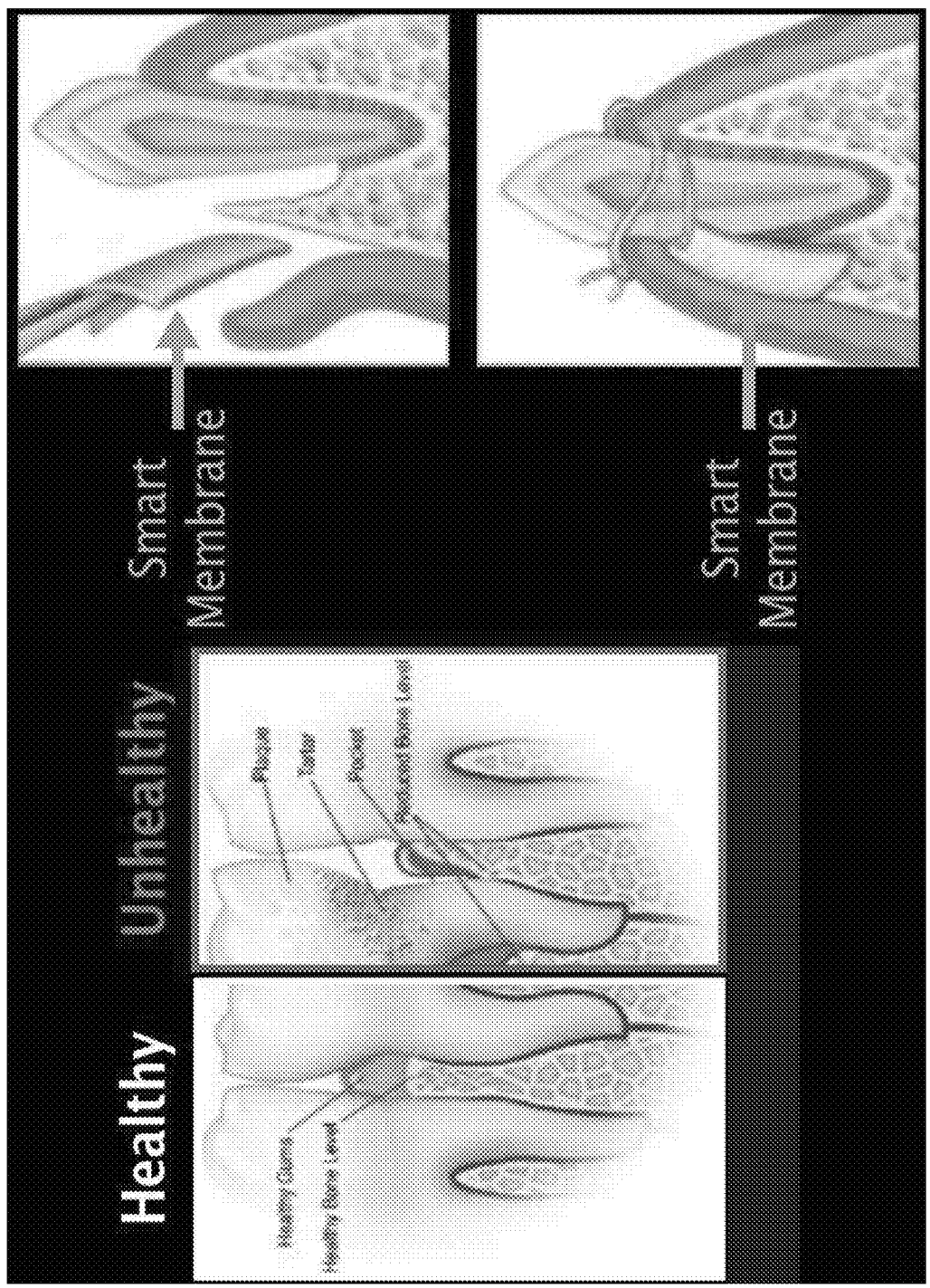
FIG. 5 depicts a schematic representation of the use of smart membrane used in periodontitis.
Figure 6:
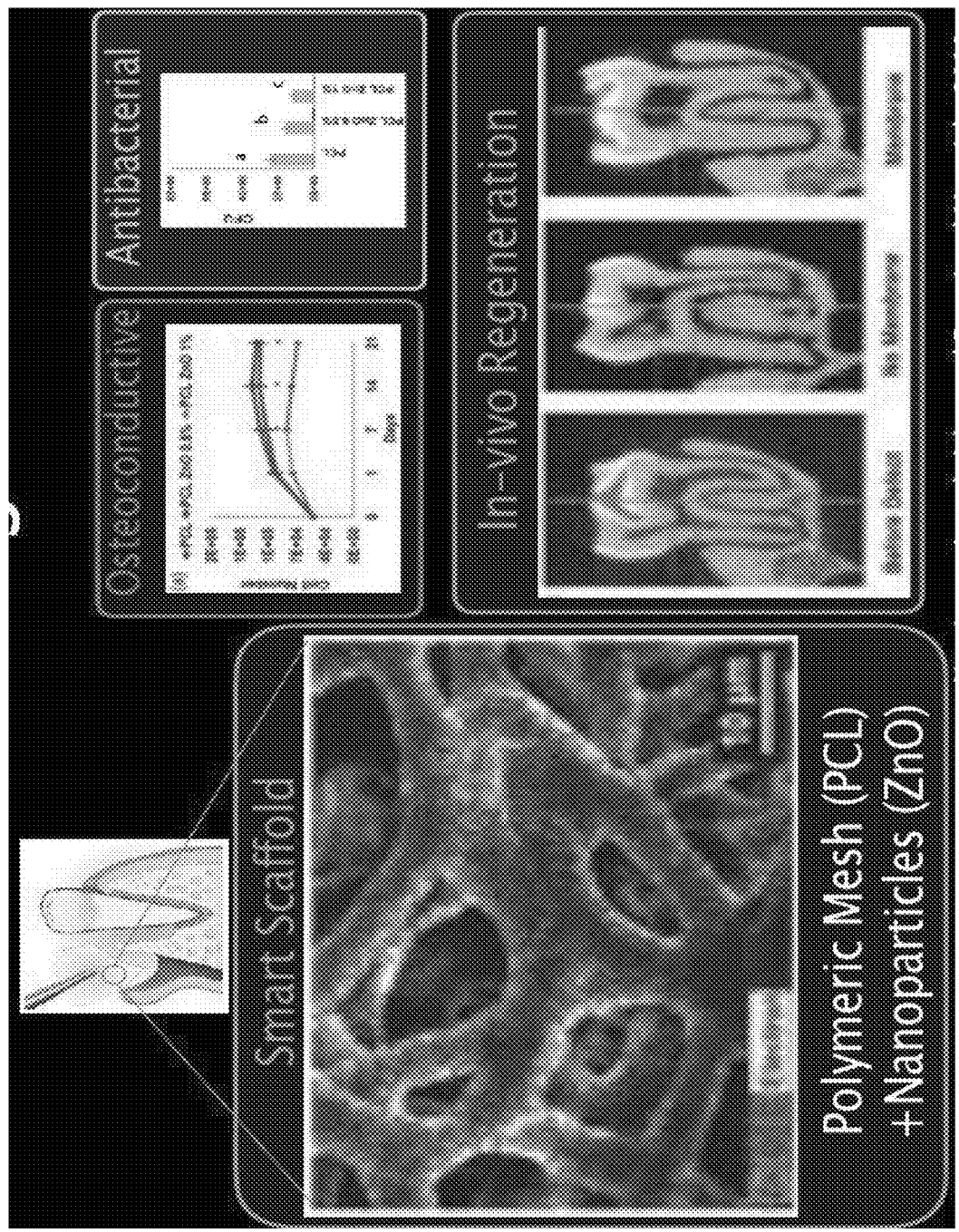
FIG. 6 depicts a schematic representation of the use of smart scaffold in periodontal regeneration.
Figure 7:
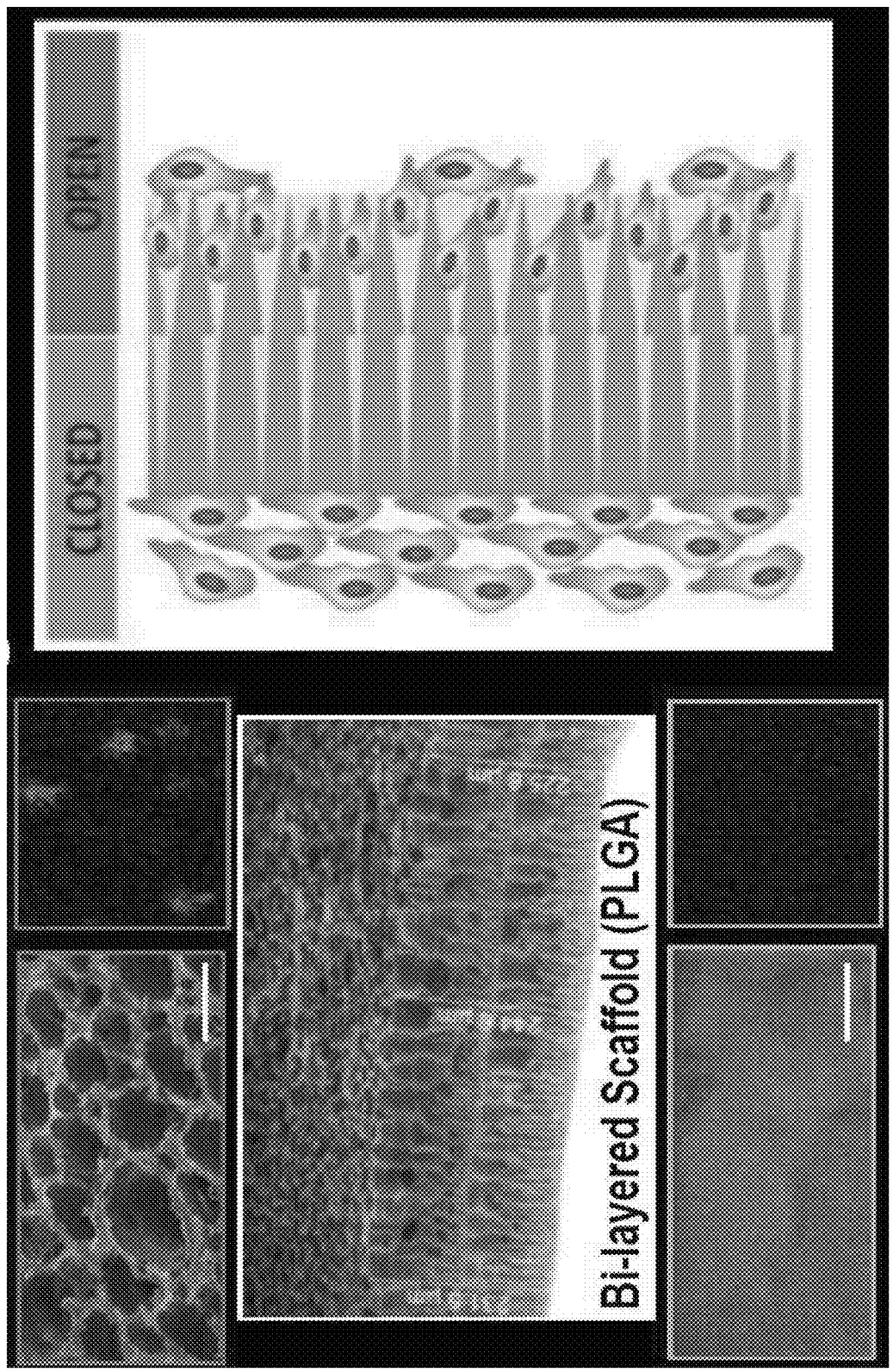
FIG. 7 depicts a schematic representation of the use of developed smart scaffold that supports the regeneration of hard tissue without additional induction factors in periodontal regeneration.
Figure 8:
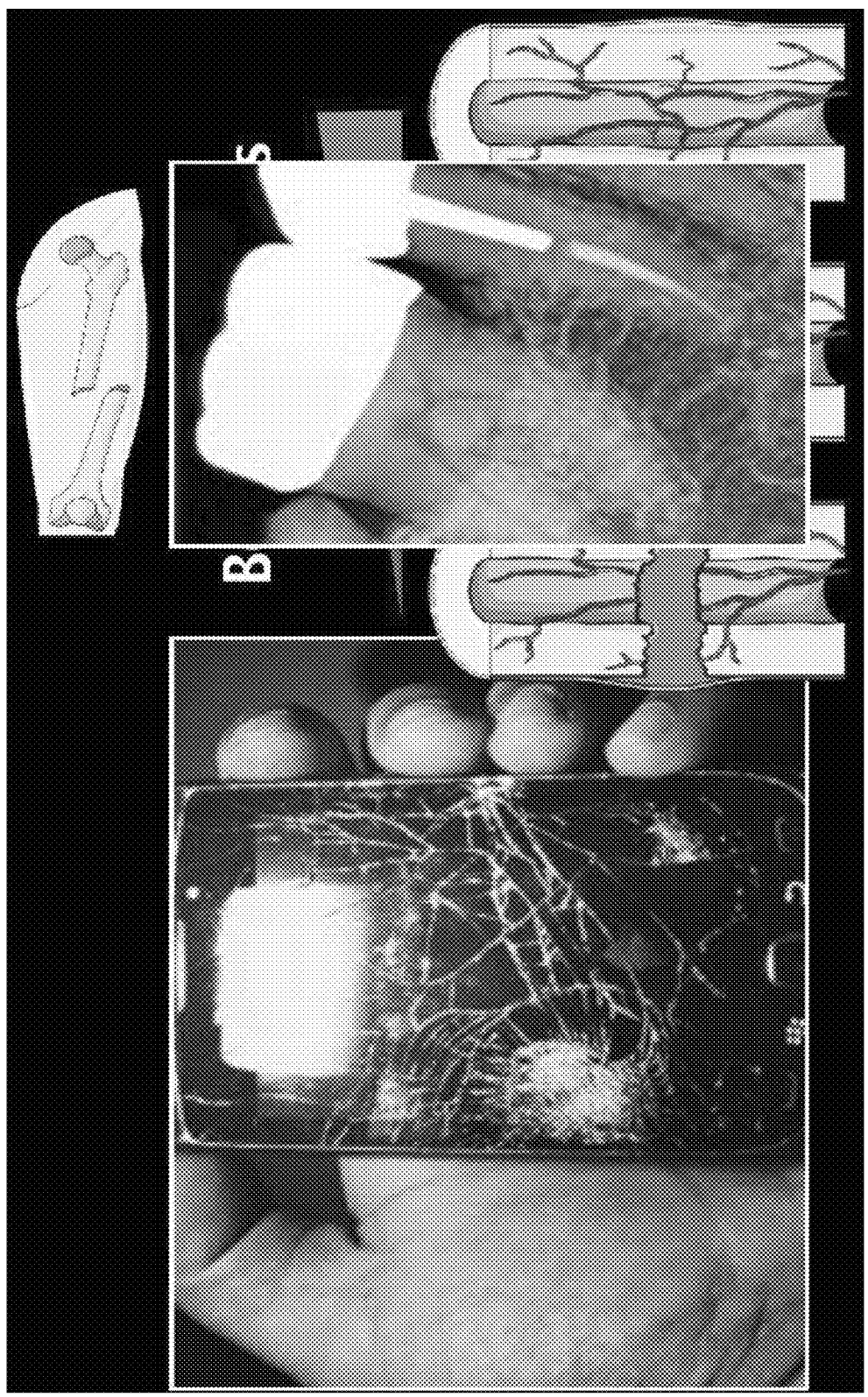
FIG. 8 depicts representative examples of failures and fractures of materials.
Figure 9:
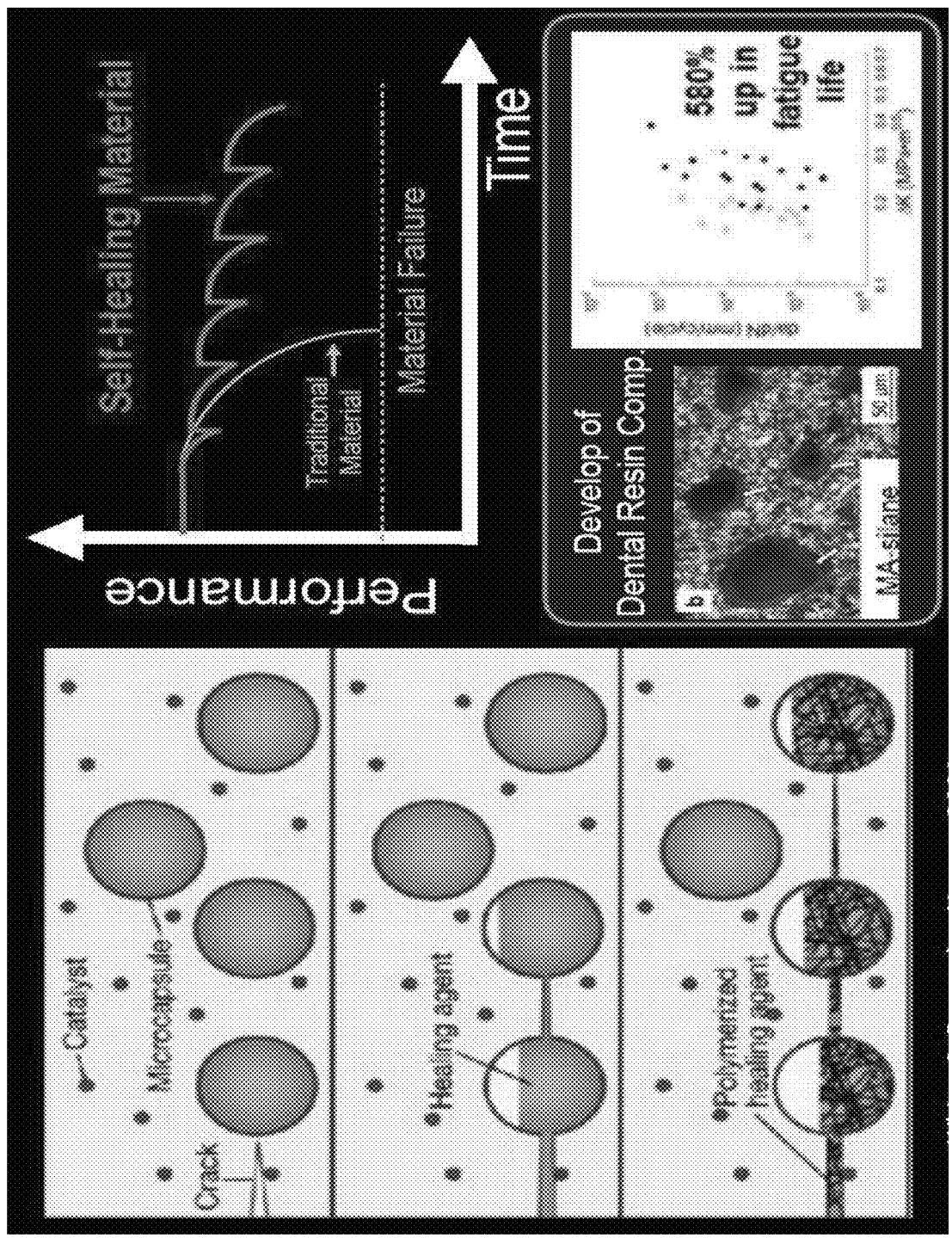
FIG. 9 depicts representative examples of properties of self-healing composites.
Figure 10:
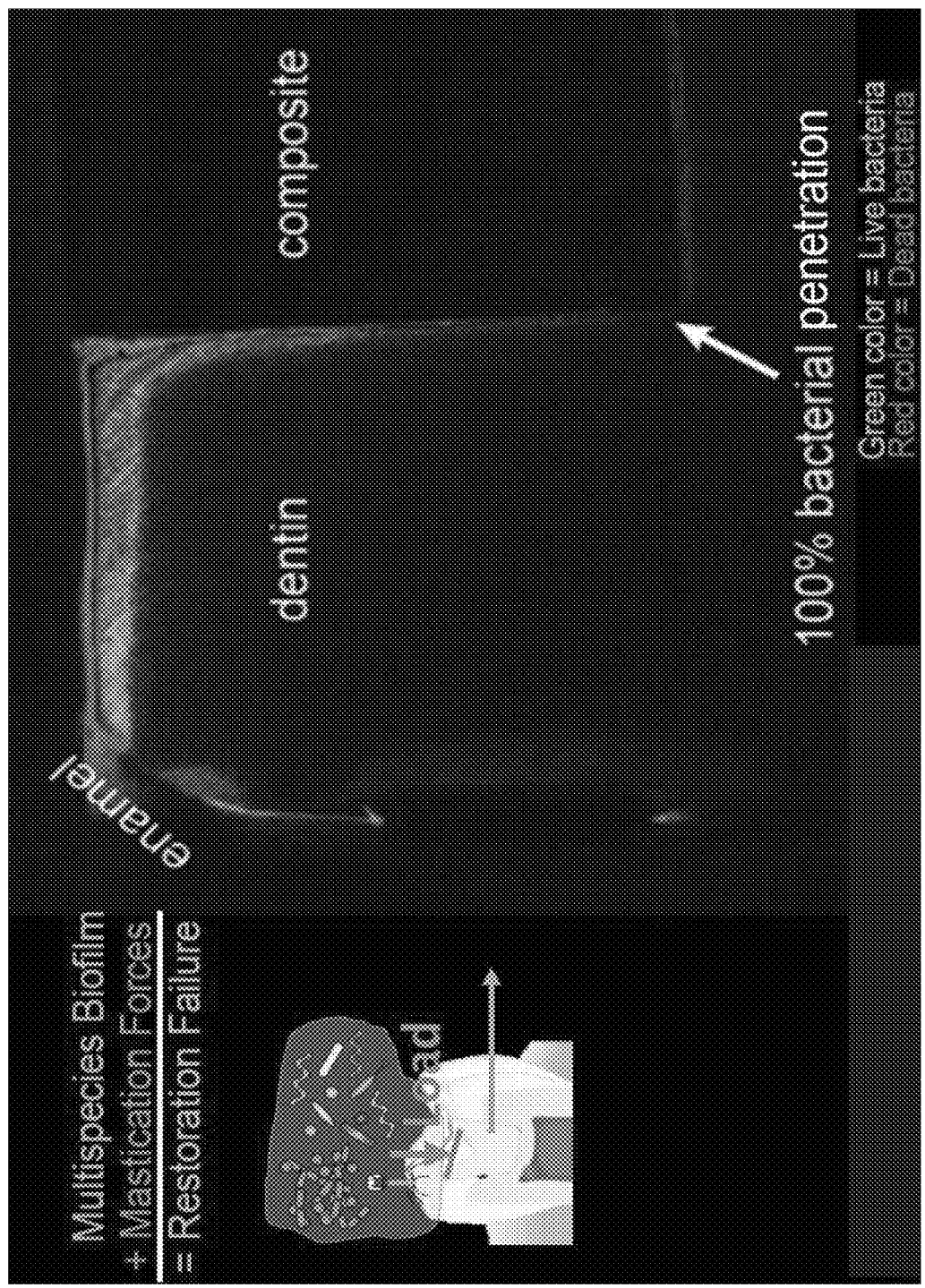
FIG. 10 depicts a representative example of resin composite restoration.

As shown in FIG. 2 and FIG. 3, dental materials are the driving force of dentistry. However, there are also several functionalities associated with smart dental biomaterials for oral health (e.g., FIG. 4). As such, it is important to note how these smart functionalities on biomaterials are applied to oral health. For example, smart membranes are used in periodontitis (FIG. 5) and smart scaffolds that support the regeneration of hard tissue without additional induction factors were developed and are used in periodontal regeneration (FIG. 6 and FIG. 7). Because materials also undergo failures and fractures (FIG. 8), it is important to investigate the properties of self-healing composites (FIG. 9) and resin composite restoration (FIG. 10).

Figure 11:
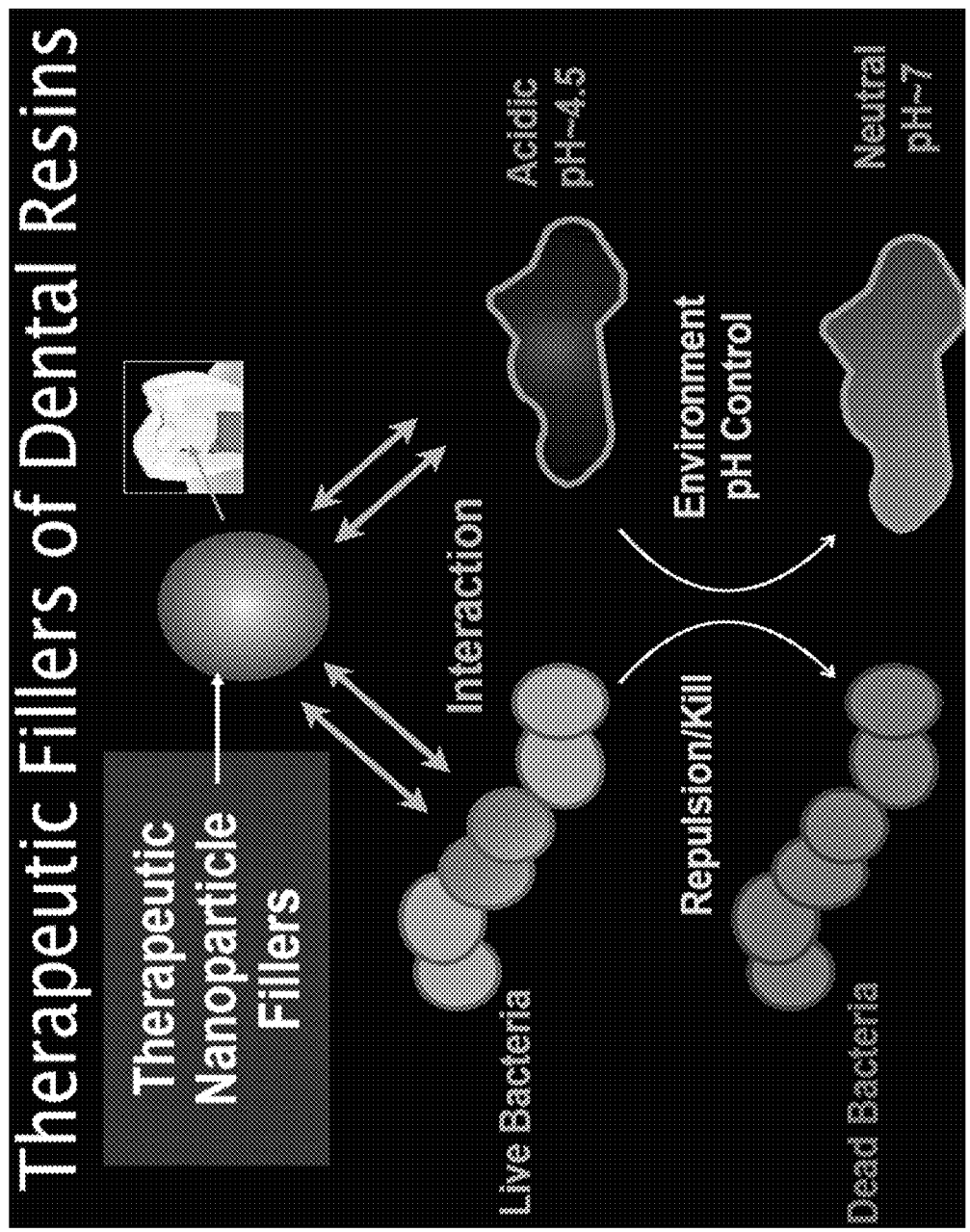
FIG. 11 depicts a schematic representation of therapeutic fillers of dental resins.
Figure 12:
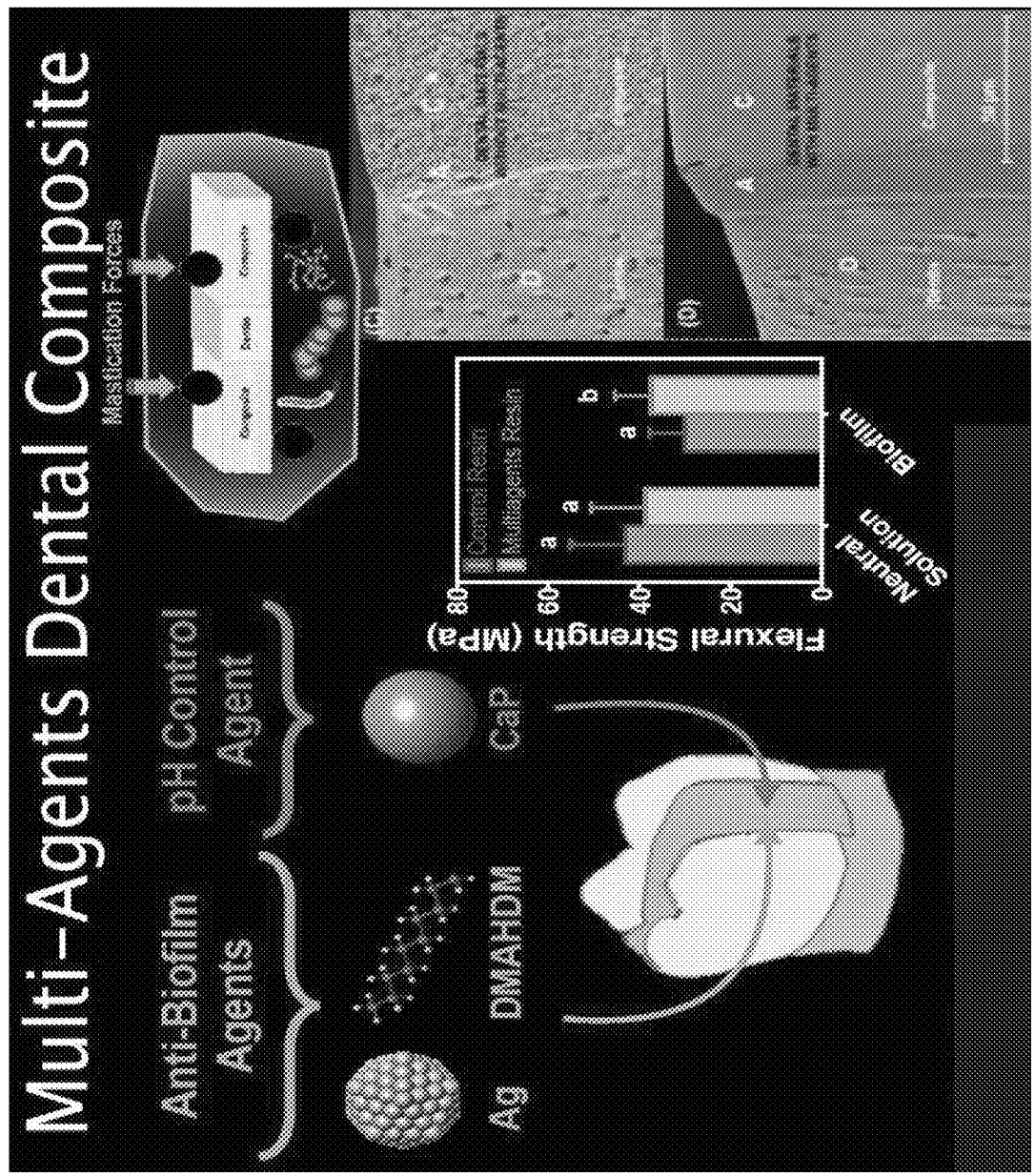
FIG. 12 depicts a schematic representation of multi-agents dental composite.
Figure 13:
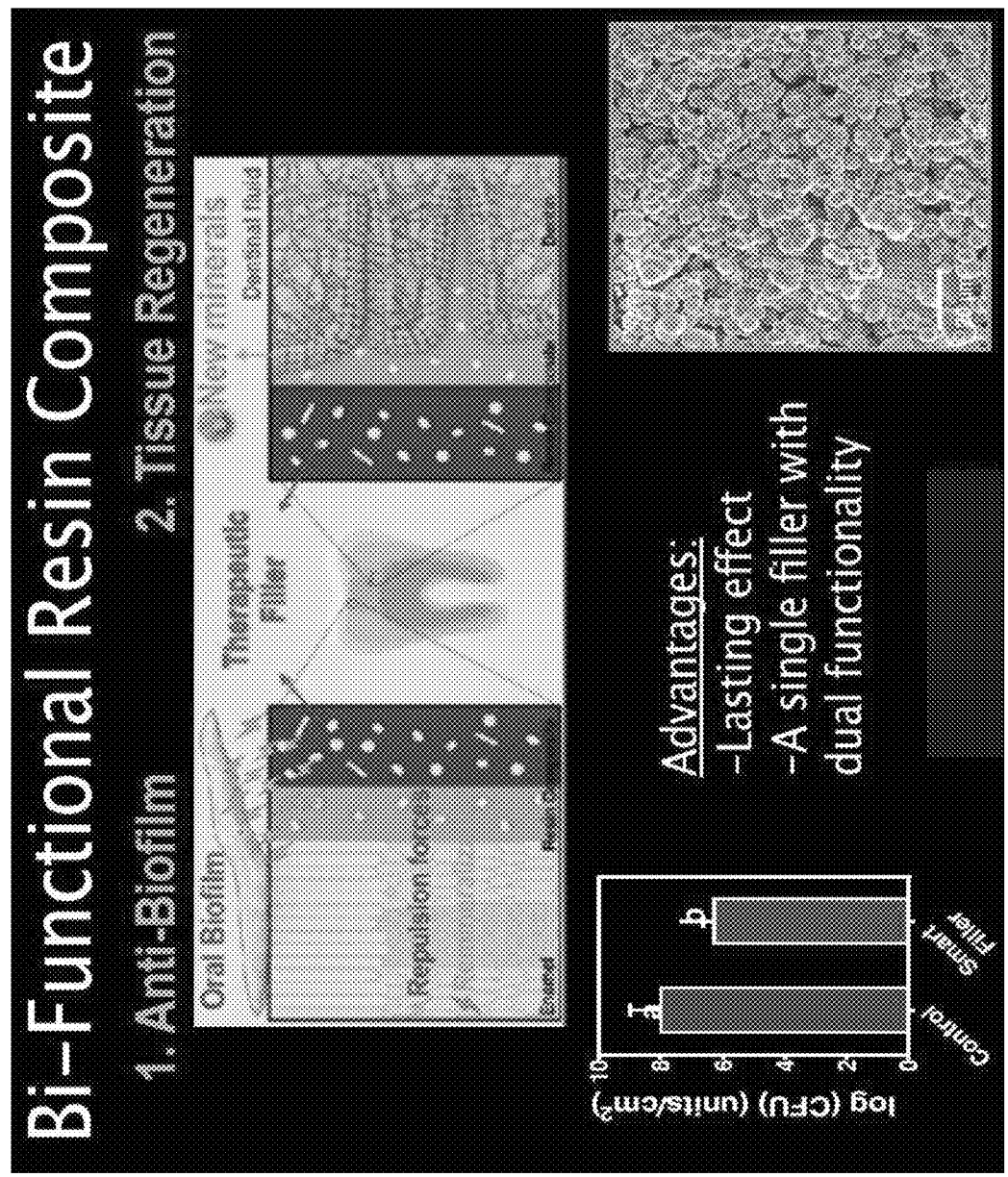
FIG. 13 depicts a schematic representation of bi-functional resin composite with lasting effect and single filler with dual functionality advantages.
Figure 14:
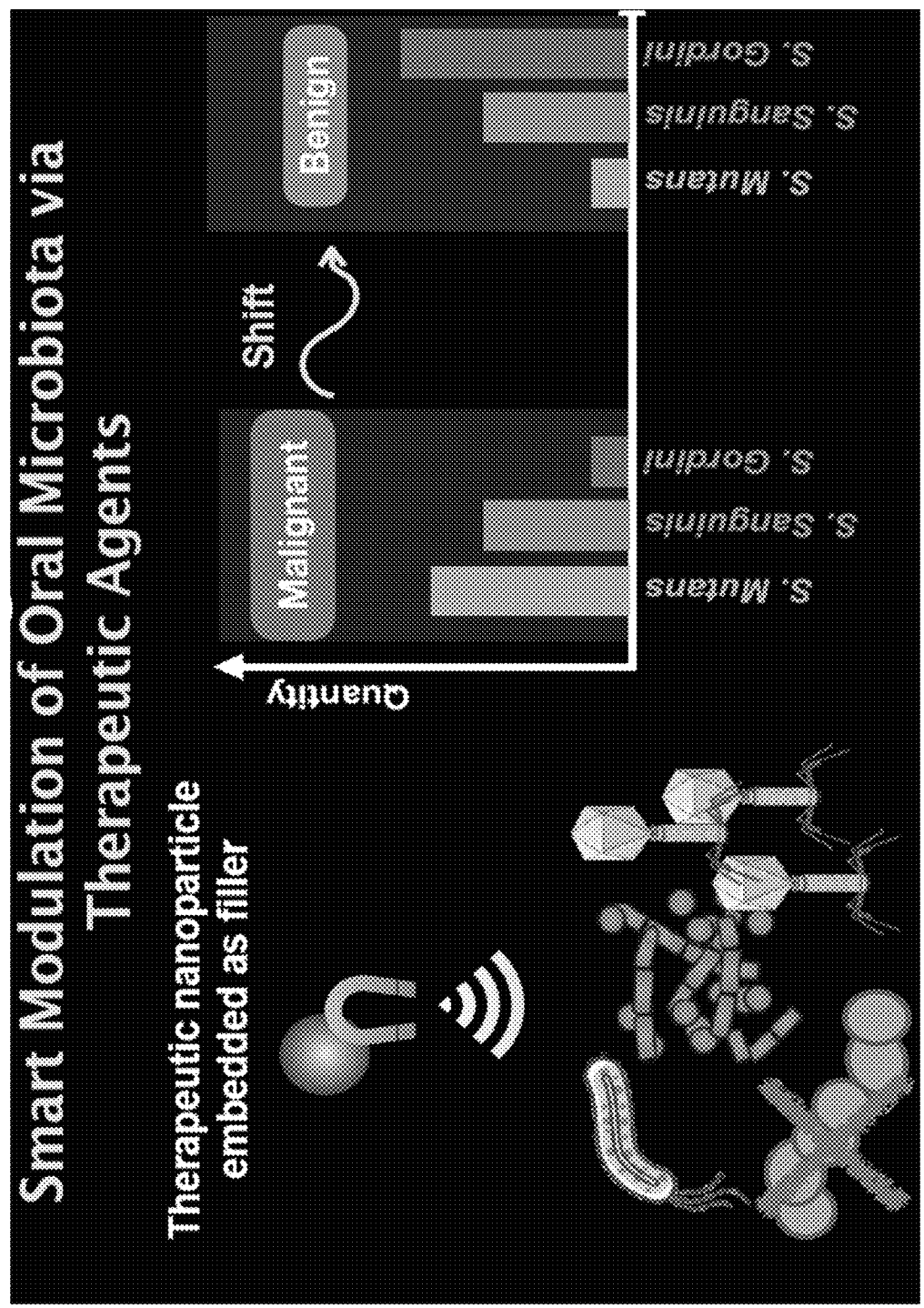
FIG. 14 depicts a schematic representation of smart modulation of oral microbiota via therapeutic agents where a therapeutic nanoparticle is embedded as a filler.
Figure 15:
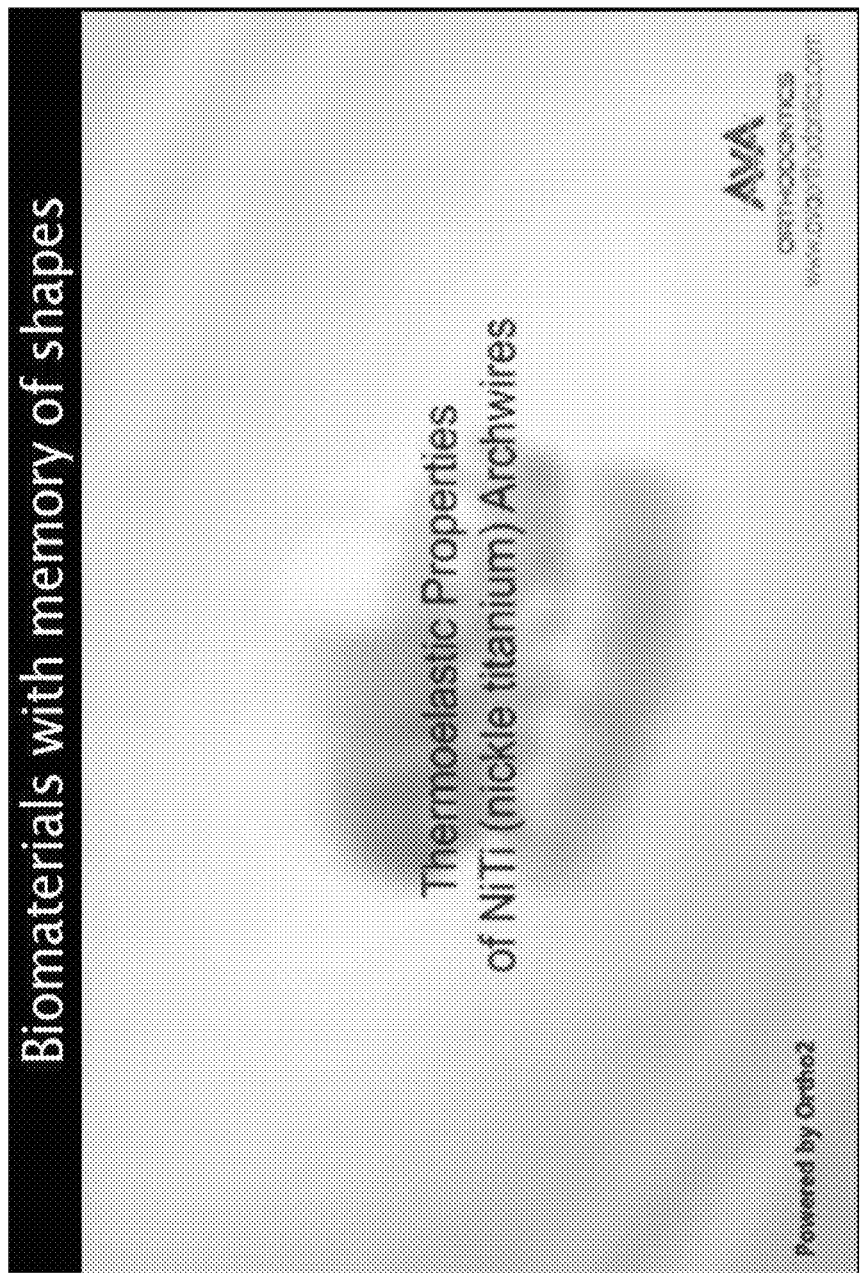
FIG. 15 depicts a representative example of smart brackets; biomaterials with memory of shapes.
Figure 16:
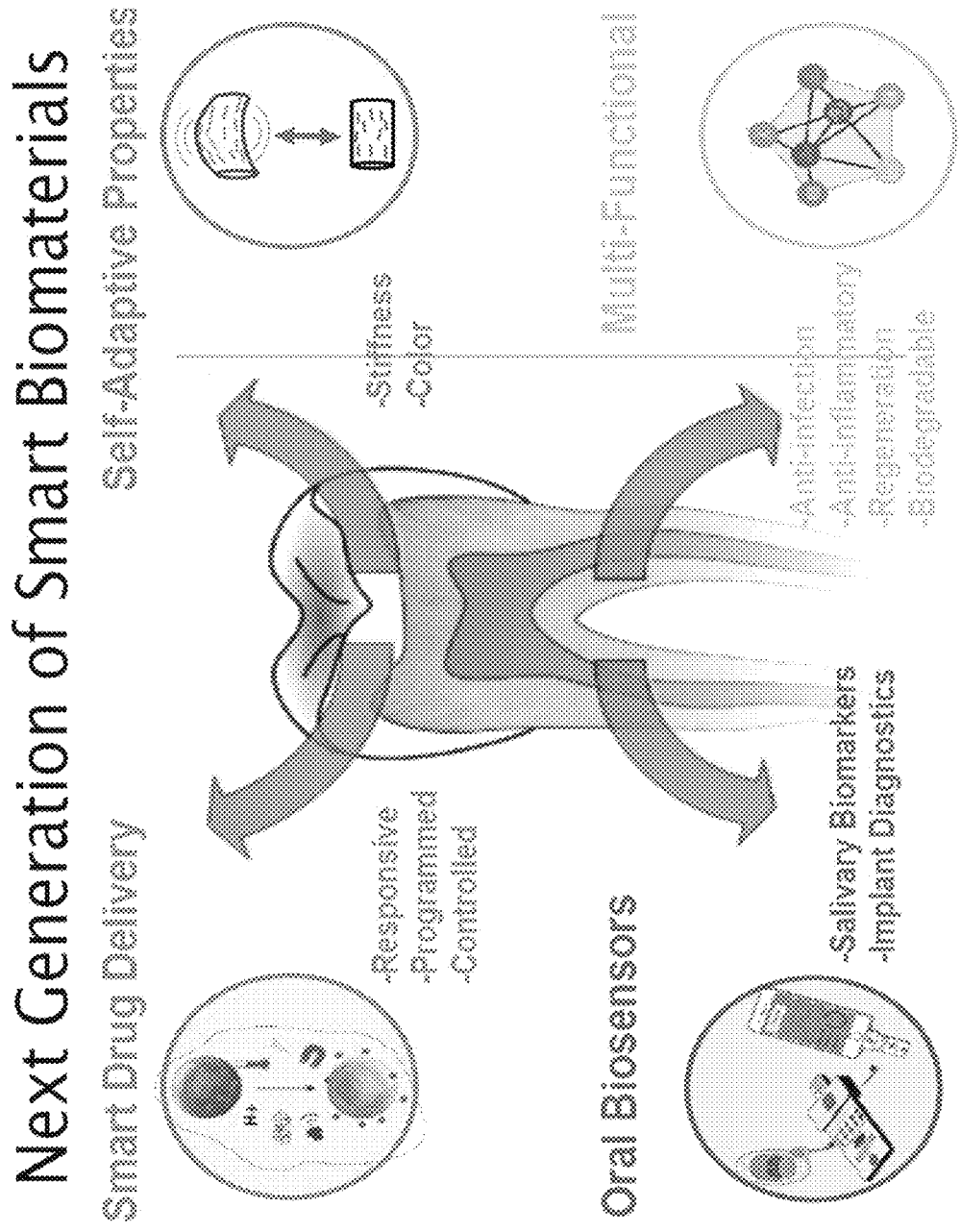
FIG. 16 depicts a schematic representation of next generation of smart biomaterials.

The present invention relates, in part to therapeutic fillers of dental resins (FIG. 11) that can be combined with multi-agents dental composites (FIG. 12) to form bi-functional resin composites with lasting effect and single filler with dual functionality advantages possessing both anti-biofilm and tissue regeneration properties (FIG. 13). For example, smart modulation of oral microbiota via therapeutic agents where a therapeutic nanoparticle is embedded as a filler reduced the amount of oral microbiota (FIG. 14). Furthermore, the next generation of smart biomaterials provides smart drug delivery (e.g., responsive, programmed, and/or controlled drug delivery), self-adaptive properties (e.g., self-adaptive stiffness and/or color), oral biosensors (e.g., salivatory biomarkers, implant diagnostics, etc.), and other multi-functionalities (e.g., anti-infection, anti-inflammatory, regeneration, biodegradable properties).

However, there are currently several challenges, such as clinical translation, foster interdisciplinary work, and reveal of generic interaction mechanisms between biomaterials and cells. Nevertheless, successful biomaterials can smartly interact with the oral environment and help improve the overall health of the subject.

Example 2: A Novel Biomaterial With Both Anti-Biofilm and Self-Remineralizing Effects Utilizing a Single Therapeutic Filler The data presented herein provides demonstrates the development of a new biomaterial with both anti-biofilm and remineralization therapeutic effects which improves the longevity of composite restorations through the. The anti-biofilm feature prevents bacteria from adhering the bonded interface thereby hindering the formation of acids and secondary caries. The remineralizing feature stabilizes the bonded interface by back-filling defective regions and neutralize low pH levels. The mechanism disclosed herein is capable of overcoming the aforementioned difficulties and increases the service life of restoration.

Specifically, the data presented herein designs a novel resin composite embedded with a single therapeutic filler capable of performing the dual function of antibiofilm and self-remineralizing the bonded interfaces and develop a realistic bonding strength evaluation method by exposing materials to simultaneous insults of oral biofilm and cyclic mastication forces, revealing the real therapeutic effects of the developed smart material on bonding strength. Electrical charges from piezoelectric fillers can repel biofilm and promote mineralization via electrostatic interactions and activated by mastication forces.

The smart biomaterial described herein repels oral bacteria thus reduces caries formation and secondary caries. The new biomaterial also regenerates tissue at the bonded interface producing better bonding between the tooth and restoration and minimizing recurrent decay. Further, this technology does not modify current operatory techniques at relatively low cost. The development of this smart biomaterial extends the clinical service life of dental restorations, saving millions of dollars annually on recurrent dental treatments while improving health outcomes for patients.

Resin-based composites are the most widely used material for dental restorations due to their outstanding aesthetics, mechanical strength and convenient clinical handling. However, their average clinical lifespan is short compared to other restorative materials such as amalgam (Ferracane J et al., 2017, Journal of dental research, 96:364-371; Drummond J L et al., 2008, Journal of dental research; 87:710-719; Ferracane J L et al., 2013, Dental materials, 29:51-58; Opdam N et al., 2014, Journal of dental research, 93:943-949). The primary mode of failure for resin restorations is secondary caries due to increased accumulation of biofilms (Nedeljkovic I et al., 2018, In: Dental Composite Materials for Direct Restorations. Springer; 235-243; Busscher H et al., 2010, Journal of dental research, 89:657-665; Lin N J et al., 2017, Dental Materials; 33:667-680; Bourbia M et al., 2013, Journal of dental research; 92:989-994). The bond strength is decreased by the combined weakening effects of bacterial chemical attacks and mechanical stresses of mastication (Nedeljkovic I et al., 2018, In: Dental Composite Materials for Direct Restorations. Springer; 235-243; Khvostenko D et al., 2015, Dental Materials, 31:702-710; Jokstad A et al., 2016, Dental Materials, 32:11-25; Carvalho R M et al., 2016, Current Oral Health Reports, 3:229-233). Dental composites incorporated with ion-releasing fillers have been proposed to increase the bonding strength by preventing biofilm formation, inhibiting enzymatic degradation and promoting remineralization at faulty interfaces (Wang Z et al., 2014, Dental Materials, 30:e1-e16; Niu L et al., 2014, Dental Materials, 30:77-96; Sauro S et al., 2016, International Journal of Adhesion and Adhesives, 69:39-57). Limitations in current approaches include the depletion and leeching of fillers, reducing their efficacy to stabilize the bonded interface over time (Wang Z et al., 2014, Dental Materials, 30:e1-e16; Delaviz Y et al., 2014, Dental Materials, 30:16-32). As a result, there is a need to develop dental biomaterials with stable therapeutic fillers that can promote continuous antimicrobial and remineralizing effects over prolonged time periods.

The herein described research aims to improve the bond strength and longevity of composite restorations through the development of a new biomaterial utilizing a novel therapeutic filler with both anti-biofilm and remineralization properties. The novel composite is embedded with piezoelectric nanoparticles acting as a therapeutic agent. Mastication forces excite the filler, generating electrical charges at the material's surface. These charges simultaneously repel biofilms and precipitate new minerals from calcium-saturated solutions (e.g. dentinal fluid). The anti-biofilm feature prevents bacteria from adhering and colonizing the bonded interface thereby hindering the formation of secondary caries. The remineralizing feature stabilizes the hybrid layer back-filling faulty regions with new minerals and neutralizing low pH levels. The unique combined therapeutic effects strive to increase the longevity of implanted biomaterials, and overcome well-known limitations of current approaches, such as premature depletion and rapid degradation of unstable therapeutic agents.

Develop a Novel Biomaterial With Both Anti-Biofilm and Self-Remineralizing Effects Utilizing a Single Therapeutic Filler This section tests the hypothesis that piezoelectric charges can repel oral biofilm formation and promote the regeneration of minerals. Piezoelectric nanoparticles of Barium Titanate ($BaTiO_3$,) are incorporated in acrylic dental resins. Mechanical and electromechanical tests are conducted to characterize the physical properties of the new material. To test the anti-biofilm effect, the material is exposed to simultaneous challenges of oral biofilms and mechanical cyclic loading, and potential cells adhered to the material surface quantified. To test the remineralizing effect, the mechanically loaded material is exposed to calcium-saturated solutions, and the type and quantity of minerals are assessed. An optimal material formulation is determined based on mechanical, anti-biofilm and remineralizing therapeutic effects.

Dental Caries: Oral health is an essential indicator of overall health, well-being and quality of life. Common oral diseases include caries, periodontal disease, erosion, abfraction lesions and oral cancer (Organization WH, et al., Oral health. Fact sheet No. 318. Geneva. World Health Organization; 2012; US Department for Health and Human Services. Oral health in America: A report of the Surgeon General, Rockville, MD: US Department of Health and Human Services, National Institute of Dental and Craniofacial Research. National Institutes of Health; 2000; Kassebaum N et al., 2015, Journal of dental research, 94:650-658). Tooth decay remains a major problem in dental health (Kassebaum N et al., 2015, Journal of dental research, 94:650-658). The Global Burden of Disease Study (2016) estimated that 2.4 billion people suffer from caries of permanent teeth with 486 million children suffering from caries (Vos T et al., 2016, The Lancet., 388:1545-1602). There is mounting evidence that caries is a growing concern in the aging populations (Fejerskov O, Kidd E. Dental caries: the disease and its clinical management. 3rd ed. John Wiley & Sons; 2015, Ch. 18) and in underserved populations (Federation WD. The challenge of oral disease: a call for global action: the oral health atlas. Word Dental Federation Btighton; 2015). There is a global need to develop new technologies, biomaterials and policies that further prevent tooth decay and improve health. Restorative Dental Materials: Placement and replacement of fillings remains the most common procedure in general dentistry representing an enormous annual expense (Mjör I A et al., 2008, Journal of the American Dental Association, 139:565-570; Clarkson J et al., 2000, Journal of dentistry. 2000; 28:233-239; Sunnegårdh-Grönberg K et al., 2009, Journal of dentistry, 37:673-678). In fact, replacing failed restorations accounts for 50-70% of all clinical work (Beazoglou T et al., 2007, Public Health Reports, 122:657-663). It has been estimated that approximately 122 millions tooth restorations are performed in the U.S. every year (Beazoglou T et al., 2007, Public Health Reports, 122:657-663). The use of amalgam has become less popular due to its aesthetically unappealing color, criticized biocompatibility and deleterious environmental impact (Lynch C D et al., 2014, Journal of dentistry, 42:377-383).

Resin-based composites are increasingly used for the restoration of teeth (Beck F et al., 2015, Dental Materials, 31:958-985). However, their annual failure rate is higher than for amalgam in posterior restorations (Ferracane J et al., 2017, Journal of dental research, 96:364-371; Sarrett D C et al., 2005, Dental Materials, 21:9-20; Bernardo Metal., 2007, The Journal of the American Dental Association, 138:775-783; Kopperud S E et al., 2012, European journal of oral sciences, 120:539-548). The average lifespan of dental resin composites is only 7 years (Ferracane J L et al., 2013, Dental materials, 29:51-58; Opdam N et al., 2014, Journal of dental research, 93:943-949). Failure is particularly prevalent for Class V restorations where mechanical stresses and biofilm formation are highest (Zhang N et al., 2016, Materials, 9:888). The two main reasons for restored tooth failure are secondary caries and fractures (Nedeljkovic I et al., In: Dental Composite Materials for Direct Restorations. Springer; 2018, 235-243.; Beck F et al., 2015, Dental Materials, 31:958-985; Ástvaldsdóttir Á et al., 2015, Journal of dentistry, 43:934-954). The major drawback of resin-based restorations is their increased accumulation of biofilms when compared to other dental materials such as amalgam (Busscher H et al., 2010, Journal of dental research, 89:657-665; Lin N J et al., 2017, Dental Materials; 33:667-680; Bourbia M et al., 2013, Journal of dental research; 92:989-994). The strength of the bonded interface is reduced due to the synergy between chemical and mechanical attacks. Acidogenic bacteria from biofilms produce acid that degrades the dental tissue, and in combination with cyclic stresses from mastication, weakens the bonded interface and restoration failure occurs (Nedeljkovic I et al., 2018, In: Dental Composite Materials for Direct Restorations. Springer; 235-243; Khvostenko D et al., 2015, Dental Materials, 31:702-710; Jokstad A et al., 2016, Dental Materials, 32:11-25; Carvalho R M et al., 2016, Current Oral Health Reports, 3:229-233).

Few strategies have been proposed to limit biofilm accumulation and prevent tissue degradation (Wang Z et al., 2014, Dental Materials, 30:e1-e16; Delaviz Y et al., 2014, Dental Materials, 30:16-32). To repel/kill oral bacteria, dental composites have been incorporated with agents such as silver, quaternary ammonium, 12-methacryloyloxydo-decylpyridinium bromide, zinc-oxide, carboxybetaine, among others. Antimicrobial mechanisms include the disruption of enzyme systems, inhibition of sugar metabolism and electrostatic interactions between cell and biomaterial surface (Wang Z et al., 2014, Dental Materials, 30:e1-e16; Delaviz Y et al., 2014, Dental Materials, 30:16-32; Santos M R et al., 2016, Materials, 9:599). To mitigate acid production, composites have been embedded with amorphous calcium phosphates. Localized acidic pH levels are neutralized via ionic chemical exchange (Melo M A et al., 2016, ACS applied materials & interfaces, 8:11779-11787; Weir M et al., 2012, Journal of dental research, 91:979-984). To inhibit enzymatic degradation, agents such as chlorhexidine, galardin, and benzalkonium chloride have been incorporated into the resin blends (Mazzoni A et al., 2015, Journal of dental research, 94:241-251). To remineralize and stabilize the hybrid layer, ion-releasing agents have been incorporated to resins with bioactive glasses, calcium phosphates and fluoride (Niu L et al., 2014, Dental Materials, 30:77-96; Sauro S et al., 2016, International Journal of Adhesion and Adhesives, 69:39-57). Diffused ions serve as precursors that remineralizes faulty hybrid layers by back-filling comprised regions. These therapeutic approaches have major limitations including depletion and leaching of the therapeutic fillers reducing their efficacy to stabilize the bonded interface over time. As a result, there is a need to design composites with long-lasting therapeutic agents that help remineralize bonded interfaces and repel/kill biofilms. With millions of restorations performed each year, continuing research and successful clinical implementation of novel materials are critical to the improvement of oral health.

Bonding strength evaluation methods are available for understanding the behavior and improving the clinical performance of dental materials (Ilie N et al., 2017, Dental Materials, 33:880-894; Armstrong S et al., 2017, Dental Materials, 33:133-143). Generally, laboratory tests are simple, static and are conducted under ideal conditions. In fact, the dental materials community has recognized numerous shortcomings to these evaluation methods (Betamar N et al., 2007, Journal of Adhesive Dentistry, 9; Raposo L H et al., 2012, Dental materials, 28:e50-e62; Spencer P et al., 2010, Annals of biomedical engineering, 38:1989-2003). Dental restorations are subjected to oral environments with complex biochemical interactions and cyclic loading from mastication. Mimicking these fluctuating environmental conditions in a laboratory setting has been extremely difficult (Jokstad A et al., 2016, Dental Materials, 32:11-25; Kruzic J J et al., 2018, Journal of the mechanical behavior of biomedical materials; Bayne S C, 2012, Dental Materials, 28:52-71). As result, laboratory tests are not successfully predicting the behavior of dental materials during clinical service (Bayne S C, 2012, Dental Materials, 28:52-71; Liu Y et al., 2011, Journal of dental research, 90:953-968; Roulet J F, 2012, The journal of adhesive dentistry, 14:103). There have been recent efforts evaluating the bonding durability considering biofilm and the fatigue loading challenges separately (Melo M A et al., 2016, ACS applied materials & interfaces, 8:11779-11787; Silva E M et al., 2012, Journal of Biomedical Materials Research Part B: Applied Biomaterials, 100:735-741; Mutluay M M et al., 2013, Journal of the mechanical behavior of biomedical materials, 18:219-231; Li Y et al., 2014, Acta biomaterialia, 10:375-383; Carrera C A et al., 2017, Journal of dentistry, 66:62-70; Zhu L et al., 2017, Dental Materials, 33:1315-1323; Sanches L K F et al., 2017, Journal of adhesion science and Technology, 31:1386-1394). Yet, the synergism of simultaneous attacks of mechanical loading and biofilms on bonding strength has not received attention. Hence, there is a need to develop realistic bonding strength evaluation methods that closely replicates oral conditions. With the increased use of therapeutic agents in composites, continuing research on improving bonding strength evaluation methods are necessary to close the gap between lab predictions and service.

Figure 17:
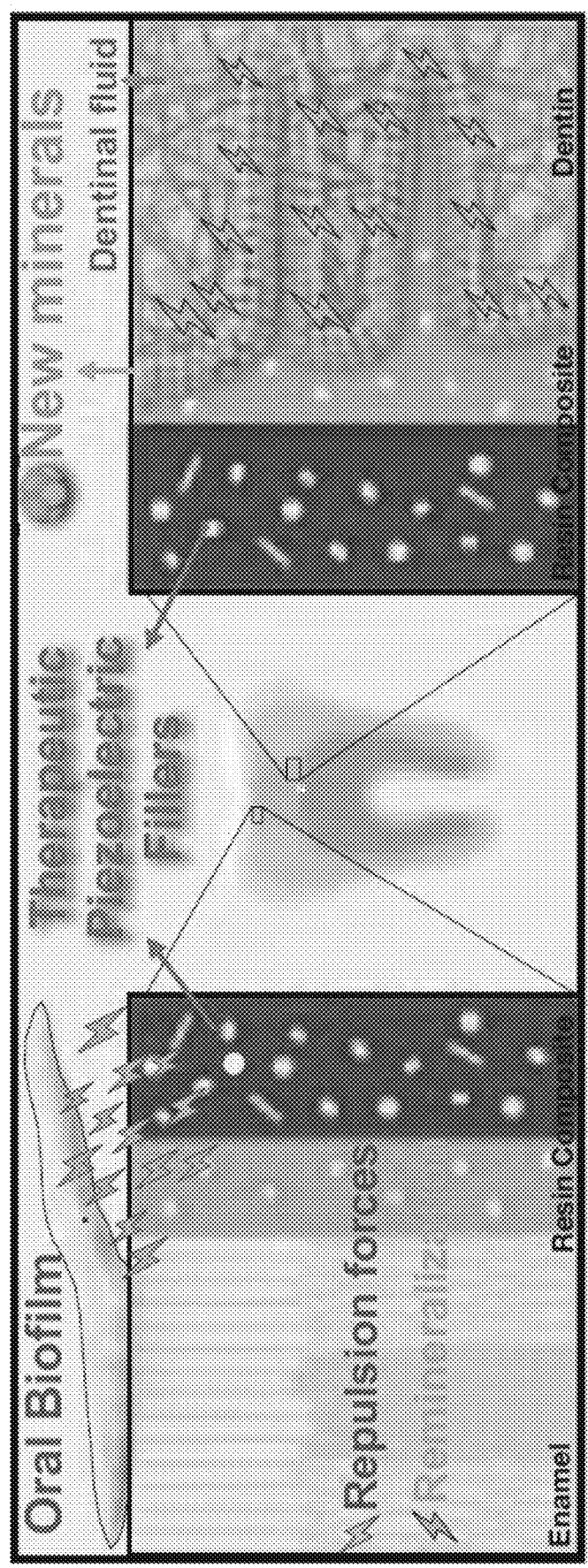
FIG. 17 depicts piezoelectric charges, activated with mastication, have dual therapeutic effects including biofilm repulsion and self-remineralization from calcium rich fluids at bonded interfaces. With a single filler to improve the service life of restorations.

To solve these challenges, a new smart composite with long-lasting anti-biofilm and self-remineralizing effects using a single therapeutic filler was developed (FIG. 17) improving the bonding strength and evaluated under realistic oral conditions. Piezoelectric charges is used as the mechanism to repel bacteria and promote mineralization. This unique approach can overcome limitations of current composites such as short-life and depletion of therapeutic effects. In addition, this research evaluates the bonding strength of the smart composite using a unique method that reproduces simultaneous challenges of oral biofilm attack and cyclic loading. The clinical service life of dental restorations is increased with this technology, saving millions of dollars on recurrent dental treatments while improving patients health. The First Unique Innovation of the Herein Described Work is the Use of Piezoelectric Materials as a Single Therapeutic Filler With Anti-Biofilm and Self-Remineralizing Effects in Dental Resins.

Electrical charges serve as the driving force for minerals to grow, and as the repulsion force to prevent bacterial adhesion at biomaterial interfaces. Mastication forces stimulate the piezoelectric material, generating therapeutic effects over the clinical life of the composite. The herein described mechanism does not rely on ion-diffusion and does not need continuous ion-recharging, since piezoelectric materials exhibit naturally long-lasting electromechanical properties (Alguero M et al., 2001, Journal of the European ceramic society, 21:1437-1440). Biofilm and caries formations are reduced and the bonding strength improved over the lifespan of the restoration. The advantages of utilizing BTO includes its low cost, commercial availability in various forms, accepted biocompatibility (Ball J P et al., 2014, Journal of Biomedical Materials Research Part A, 102:2089-2095) and radiopacity (Watts D et al., 1987, Journal of Dentistry, 15:38-43). This new mechanism could be adapted for a wide range of implantable biomaterials in need of anti-biofilm and remineralizing effects.

A second significant innovation of this work is the development of a realistic method to evaluate the bonding strength of dental materials. Bioreactors are commonly used for in-vitro studies of oral biofilms coating biomaterials in controlled laboratory settings (Li Y et al., 2014, Acta biomaterialia, 10:375-383; McBain A J et al., 2009, Advances in applied microbiology, 69:99-132; Gomes I B et al., 2018, Meireles A, Gonsalves A L, Goeres D M, Sjollema J, Simões L C, et al. 2018, Critical reviews in biotechnology, 38:657-670). However, no bonding strength evaluation method considering simultaneous cyclic loading and biofilm exposure is available. This is the first rigorous research project developing a novel dynamic bioreactor to simulate realistic oral environmental conditions to evaluate bonding strength. The use of this methodology is intended to quantify the real therapeutic effects of biomaterials exposed to the complex oral environmental and body conditions. Results are used to gain deeper understanding surrounding the failure mechanisms of the bonded interfaces. These innovations represent the first, large-scale effort to generate enhancements in the reliability and clinical longevity of restorative materials, offering significant health care benefits to the general public.

Smart Composite Preparation

The piezoelectric therapeutic agent used in this study is BTO. This compound has been used extensively in medicine due to its accepted biocompatibility and radiopacity (Ball J P et al., 2014, Journal of Biomedical Materials Research Part A, 102:2089-2095; Watts D et al., 1987, Journal of Dentistry, 15:38-43; Acosta M et al., 2017, Applied Physics Reviews, 4:041305). BTO has been used as a biomarker (Matar O et al., 2015, In: Journal of Physics: Conference Series. vol. 644. IOP Publishing, 012037), in tissue regeneration (Rajabi A H et al., 2015, Acta biomaterialia, 24:12-23) and as a biosensor (Selvarajan S et al., 2017, Biosensors and Bioelectronics, 91:203-210). However, the use of BTO for anti-biofilm and mineralization effects has not been explored. Significant advantages of BTO composites include their relatively high piezoelectric output, low-cost, facile fabrication, and white color for aesthetics (Sukumaran V et al., 2006, Trends in Biomaterials and Artificial Organs, 20:7-11; Zhang Y et al., 2014, Materials Science and Engineering: C, 39:143-149).

To prepare the dental smart composite, the previously developed methods were replicated to prepare dental composites (Melo M A et al., 2016, ACS Appl. Mater. Interfaces, 8:11779-11787) in combination with protocols for the preparation of piezoelectric composites (Li J et al., 2019, Nanoscale). In brief, commercial BTO nanoparticles (200 nm) were incorporated into dental resins with different proportions (10 to 70 wt %). The resin matrix was obtained by mixing Bisphenol A diglycidyl dimethacrylate and triethylene glycol dimethacrylate in a 1:1 ratio by weight. Camphorquinone and Ethyl 4-dimethylaminobenzoate were added as photoinitiators with 0.2 and 0.8 wt %, respectively. To facilitate homogeneous filler dispersion, mixing was conducted using a planetary mixer (FIG. 18A). Samples were fabricated via molding and the mixture was light-cured for 1 min using a LED unit. A control group was created using traditional silicon oxide ($SiO_2$) fillers with similar particle size (300 nm).

Representative samples (beam and cylinder) obtained with the developed protocol are shown in FIG. 18B. The smart composite's microstructure showed the therapeutic fillers properly dispersed within the matrix with some isolated agglomerations of sizes of 50 and 7 µm (FIG. 18C).

Mechanical Characterization

The flexural strength of the smart composites and control groups with different filler quantities were measured according to the ISO 4049 (Dentistry—Polymer-based restorative materials. Geneve: International Organization for Standardization. 2009). Rectangular beams with cross section of 2×2 $mm^2$ and length of 25 mm were prepared. The specimens were subjected to quasi-static loading under a 3-point bending configuration using a universal testing system. The flexural strength was calculated according to $\sigma_y=3Pl/bh^2$, where l is the distance between exterior supports (20 mm), P is the load, b is the width and h is the thickness of the sample. The flexural modulus was calculated according to $E=l^3m/4bh^3$.

Figures 19A, 19B:
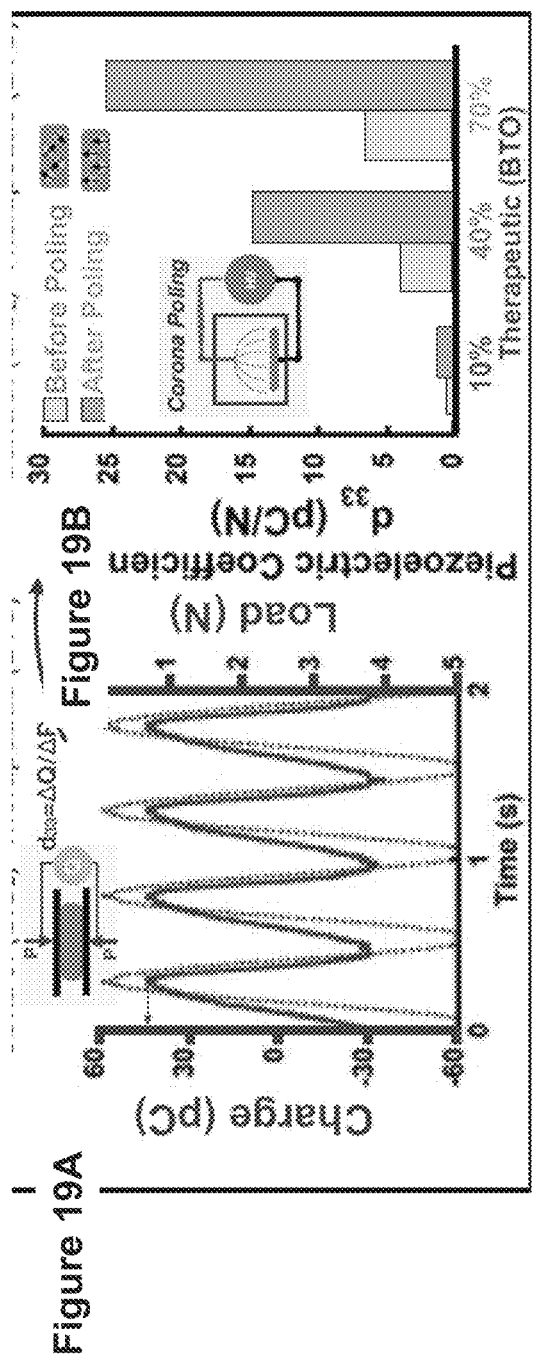
FIG. 19A and FIG. 19B, depicts representative examples of mechanical and electromechanical evaluation of the novel composite.

The flexural strength of the smart piezoelectric composite ranged from 50 to 80 MPa whereas the control with $SiO_2$ fillers averaged 75 MPa (FIG. 19A and FIG. 19B). The flexural modulus for the smart and control groups (FIG. 19A and FIG. 19B) ranged from 1-3 GPa with similar trends. The inset was a representative stress-strain curve for the smart composite with 40% of BTO filler. In general, the mechanical properties were proportional to the filler quantity for both groups and were in compliance with the ISO 4049 ($\sigma_y>50$ MPa). The obtained responses for strength and modulus of the new composite were comparable with different commercial dental resins composites (Ferracane J L et al., 2011 Dental materials, 27:29-38).

Electromechanical Characterization

Piezoelectric materials are capable of stimulating the physiological electrical micro-environments (Tandon B et al., 2018, Acta biomaterialia). These electrical charges play a vital role on biofilm repulsion and remineralization effects. To evaluate the electromechanical performance of the smart composites, cylinders were fabricated replicating developed methods (Orrego S et al., 2017, Applied Energy, 194:212-222). To measure the electrical charge, standard characterization method (i.e. Berlincourt technique) was followed (Fialka J et al., 2012, In: Instrumentation and Measurement Technology Conference (I2MTC), 37-42) and piezoelectric coefficient ($d_{33}$) calculated. In brief, samples were loaded under dynamic sinusoidal compression. Conductive electrodes were bonded to the top and bottom surfaces of the sample. Electrical charges (Q) were measured using a high resistance electrometer (Keithley 6517B) and signals were sent to a data acquisition instrument (NI USB 6003). The load P signal was also recorded by the data acquisition instrument, where all data was processed and peak amplitudes of P and Q calculated. The piezoelectric coefficient was estimated according to $d_{33}=\Delta Q/\Delta P$. To validate these experiments, the piezoelectric response of a commercial polymer (PVDF, TE Connectivity) was successfully measured with known $d_{33}$=33 pC/N. To improve the electromechanical response, the smart piezoelectric composite samples were subjected to corona discharge. This is a widely used process to orient the electrical dipoles of piezoelectric composites, hence increasing their electrical output (Waller D et al., 1988, Ferroelectrics, 87:189-195; Bauer S et al., 2006, IEEE Transactions on Dielectrics and Electrical Insulation, 13:953-962). To conduct corona discharge, the samples were subjected to a high electric field (15 kV/mm) under 140° C. for 1 hour (Li J et al., 2017, Nanoscale, 9:14215-14228).

The electrical response of the smart composite (40% filler) showed a positive charge generation following activation by external loading with a peak-to-peak charge of 50 pC (FIG. 19A). The piezoelectric performances ($d_{33}$) of the smart composite with three filler formulations before and after being corona poled are presented in FIG. 19B. Results showed that corona charging has a significant impact on charge generation, with a five-fold increase for the smart composite with 70% filler. The electromechanical output was proportional to the amount of filler, with the samples having the highest output being with the most filler. The obtained piezoelectric responses of the smart composite were comparable to those found in the literature ($d_{33}$=10-80 pC/N)(Mao Y et al., 2010, Journal of Applied Physics, 108:014102). The efforts showed the initial success of smart piezoelectric composites development. The present study represents the pathway to elucidate its therapeutic effects and influence on bonding strength.

Anti-Biofilm Evaluation

To evaluate the biofilm repulsion effects of the new composite, an in-vitro microcosm biofilm model that promotes cariogenic biofilm growth is replicated following previous studies (Orrego S et al., 2017, Journal of Biomedical Materials Research Part B: Applied Biomaterials, 105: 1978-1985; Cheng L et al., 2013, Journal of dentistry, 41:345-355). Sterile samples are exposed to liquid cultures of a single species of oral biofilm (*S. mutans*, ATCC® 700610). Therapeutic composites with different filler quantities are evaluated. Negative controls of $SiO_2$ composites are included. Biofilms are grown by first performing a 1:50 dilution of liquid *S. mutans* culture in fresh brain heart infusion (BHI) media. The nutrient medium to be used is enriched with sucrose in different quantities (0.2% to 4%) representing varied cariogenic diets to determine its influence on the bonding strength (Zhu L et al., 2017, Dental Materials, 33:1315-1323; McBain A J et al., 2009, Advances in applied microbiology, 69:99-132; Orrego S et al., 2017, Journal of Biomedical Materials Research Part B: Applied Biomaterials, 105:1978-1985; Rudney J et al., 2012, Journal of applied Microbiology, 113:1540-1553). The biofilm is developed aerobically to allow initial attachment and colonization over the sample (Deng D et al., 2004, Caries Research, 38:54-61). To activate the charge generation (i.e., anti-biofilm effect), samples are simultaneously loaded under compression while submerged in the cariogenic solution. Cyclic loading is conducted using a universal testing frame operated inside the incubator and attached with a vessel bioreactor to fix the samples. Mastication loading conditions are replicated. Potential growth and development of the biofilm on the surfaces of the biomaterials are assessed by different methods as follows (Azeredo J et al., 2017, Critical reviews in microbiology, 43:313-351). To evaluate viability of the biofilm, confocal laser scanning microscopy imaging is performed with commercially available nucleic acid dyes (SYTO-9) (LIVE/DEAD BacLight, Molecular Probes), which are widely accepted in the oral microbiology field (Khvostenko D et al., 2015, Dental Materials, 31:702-710; Melo M A et al., 2016, ACS Appl. Mater. Interfaces, 8:11779-11787; Tawakoli P et al., 2013, Clinical oral investigations, 17:841-850). Fluorescence allows for visualization of cell distribution along the material surface (FIG. 20A). Quantification of the cells is measured using the BioFilmAnalyzer software tool (Bogachev M I et al., 2018, PloS one, 13:e0193267). High amounts of dead bacteria reveal the inhibition of biofilm colonization. Colony-forming units (CFU) tests are also conducted to determine the number of bacteria able to grow providing further analysis of biofilm repulsion (FIG. 20B).

To quantify the biofilm biomass, the biofilms are stained with crystal violet (CV) (O'Toole GA, 2011, Journal of visualized experiments: JoVE, 47; Merritt J H et al., 2011, Current protocols in microbiology, 22:1B-1; Wang L et al., 2016, Dental Materials, 32:e351-e361), a dye that binds to surface molecules and the extracellular matrix. Adherent cells are stained with CV and resuspended in acetic acid. The absorbance of the resuspended solution is measured and the biofilm biomass is calculated (Pitts B et al., 2003, Journal of microbiological methods, 54:269-276) (FIG. 20C). The biomass of biofilms on smart composites is much lower values than that of control composites.

To evaluate the metabolic activity of biofilms, a MTT assay is conducted, measuring the enzymatic reduction of MTT to formazan via microplate reader (Ionescu A C et al., 2017, Journal of Materials Science: Materials in Medicine, 28:108). Previously described methods are followed to conduct the metabolic assay (Zhang K et al., 2013, Journal of Dentistry, 41:504-513). Results are displayed as optical density (OD) and the metabolic activity is higher for control groups. Moreover, the acid produced by biofilms changes the surface topography of the material (Verran J et al., 2001, Biofouling, 17:59-71). To quantify these physical changes, roughness tests are conducted following previous protocols (Orrego S et al., 2017, Applied Energy, 194:212-222). To show no attachment of biofilm to the material's surface, a decreased roughness is reported.

Figure 25:
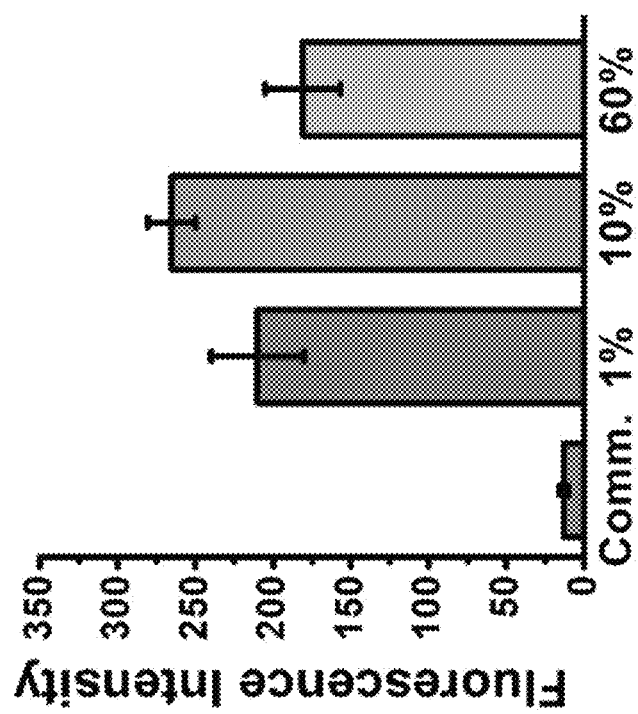
FIG. 25 depicts representative results for reactive oxygen species (ROS) for different quantities of BTO Composite samples under mechanical load stimulation as proof of the antibacterial mechanism (N=5 for each).
Figure 26:
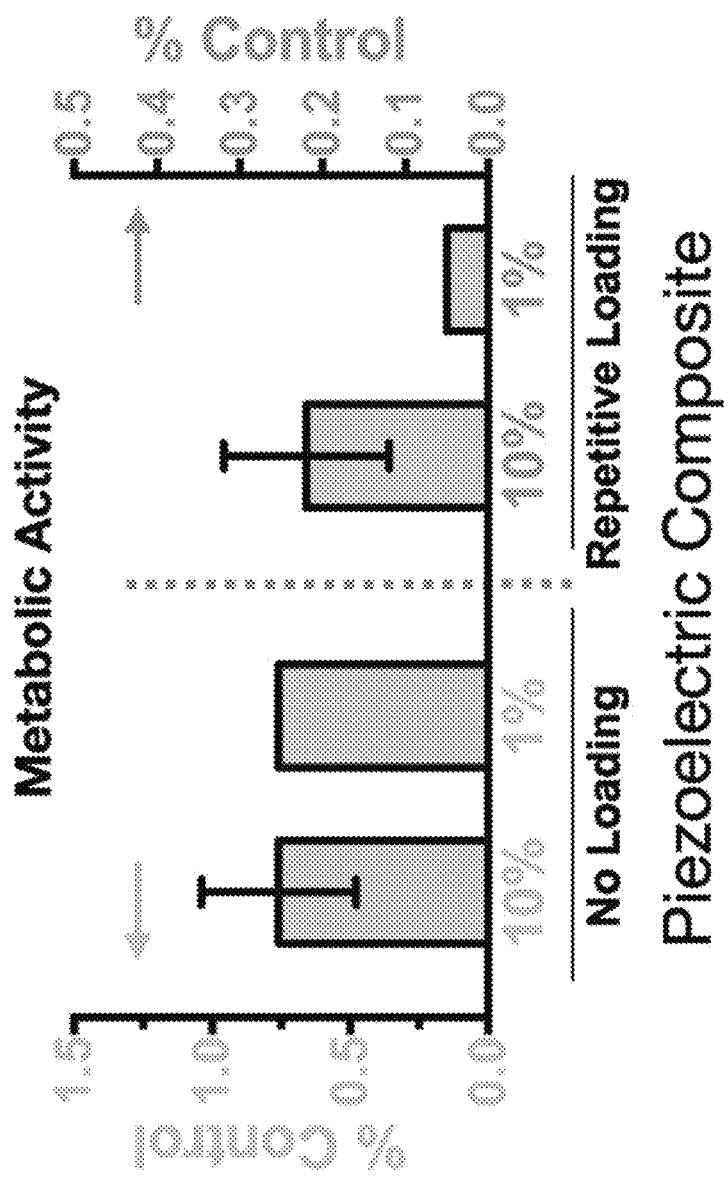
FIG. 26 depicts representative results demonstrating the influence of BTO quantity on antibacterial effect (i.e. metabolic activity).
Figure 27:
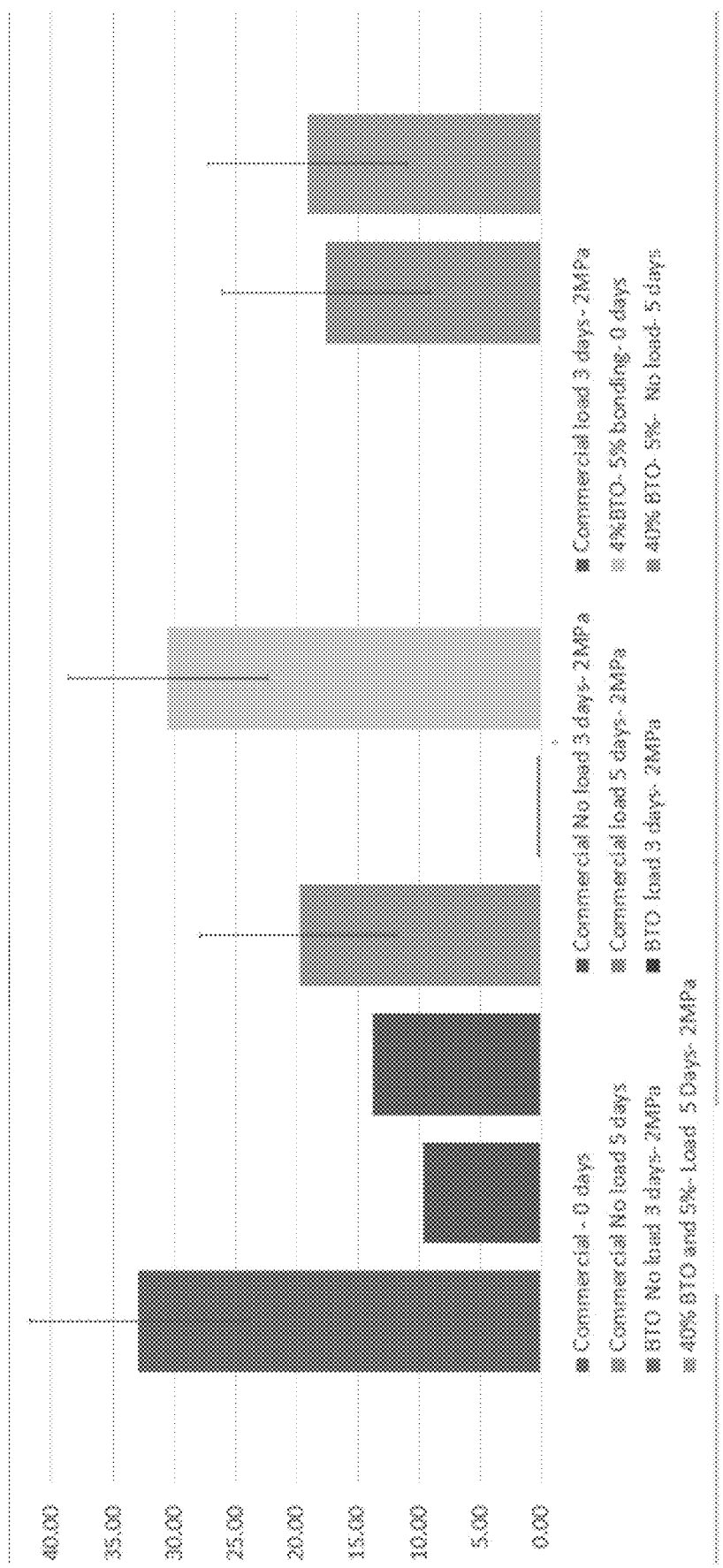
FIG. 27 depicts representative results demonstrating bonding strength data of commercial and piezoelectric composites under different environmental conditions.

Anti-biofilm Mechanism: Electrostatic forces are among the earliest interactions that influence the attachment of bacterial cells to surfaces (Renner L D et al., 2011, MRS bulletin, 36:347-355; Tuson H H et al., 2013, Soft matter, 9:4368-4380; Römling U et al., 2012, Journal of internal medicine, 272:541-561). S. mutans biofilm membrane is negatively charged (Zhang Z et al., 2011, Antimicrobial agents and chemotherapy, 55:1075-1081). Hence, a negatively charged surface is more resistant to bacterial adhesion due to repulsion electrostatic forces (Song F et al., 2015, Journal of dental research, 94:1027-1034). Piezoelectric charges repelled bacteria and prevented adhesion and growth of oral biofilms via electrostatic interactions (FIG. 25).

Self-Mineralization Evaluation

To evaluate the mineralization effects of the smart piezoelectric composite, an in-vitro model simulating calcium-rich environments is developed based on well-established methods (Mann S, 2001, Biomineralization: principles and concepts in bioinorganic materials chemistry. vol. 5. Oxford University Press on Demand; Eliaz N et al., 2017, Materials, 10:334). Smart composites are incubated in supersaturated solutions of simulated body fluid (SBF) for up to 14 days at 37° C. SBF contains calcium and phosphate ions required for mineralization. Different artificial solutions, representing saliva (Baumann T et al., 2017, Scientific reports, 7:12999) and dentinal fluid (SDF) (Özok A et al., 2004, Journal of dental research, 83:849-853), are also used. To investigate how piezoelectric charges promote nucleation and mineral growth, smart composites are submerged in the saturated solutions. Composites with varying amounts of fillers are evaluated. Cyclic loading is conducted using a testing frame operated inside the incubator and with samples attached in the liquid mineral saturated container. The negative surface of the composite is monitored because the negative charges drive mineralization. The amount of precipitated mineral is quantified using a profilometer (step-height) and visually using microscopy (FIG. 20D). Chemical analysis is employed to determine the mineral crystallinity, phase and structure (Vallet-Regi M et al., 1999, Journal of Biomedical Materials Research: An Official Journal of The Society for Biomaterials, The Japanese Society for Biomaterials, and The Australian Society for Biomaterials, 44:416-421). Energy Dispersive X-Ray Spectroscopy results provide peaks corresponding to the calcium (Ca) and Phosphate (P) elements and as well as the atomic Ca/P proportion. X-ray Diffraction patterns confirm the mineral phase (Dorozhkin S V, 2012, Acta biomaterialia, 8:963-977).

Mineralization Mechanism: In general, biomineralization is based on electrostatic interactions between organic and inorganic phases (Mann S, 2001, Biomineralization: principles and concepts in bioinorganic materials chemistry. vol. 5. Oxford University Press on Demand). In matrix-mediated mineralization, minerals nucleate/grow from calcium-saturated solutions onto surfaces with tailored chemistry including different types of anionic functional groups (e.g. carboxyl), charged amino acids, and phospholipids (Kepa K et al., 2015, Biosurface and Biotribology, 1:214-227; Tofail S A et al., 2016, Advanced Materials, 28:5470-5484). The negative charges promote mineralization by establishing local calcium-ion supersaturation via electrostatic charges (Veis A, 2003, Reviews in mineralogy and geochemistry, 54:249-289). Negative electrostatic forces obtained via piezoelectric activity act as novel mechanisms for mineralization from Ca saturated environments, and anti-biofilm therapeutic effect.

The herein described studies assess the therapeutic anti-biofilm and self-remineralizing effects of piezoelectric charges. A potential limitation is the low magnitude of the charges and subsequent inability to achieve sufficient electrostatic force. To increase the electromechanical performance, BTO nanowires is used as well as additional conductive $TiO_2$ fillers (Salim M et al., 2018, Journal of Intelligent Material Systems and Structures, 29:2105-2121). These fillers improve the electrical properties of the composite, enhancing both its conductivity and capacitance. To improve the strength and modulus of the composite ($\sigma_y$>80 MPa), the addition of coupling agents (e.g. silane, dopamine) and enhancement of mixing techniques (e.g. ethanol evaporation) are also considered.

Example 3: Evaluation of Piezoelectric Nanoparticles

Three of the biggest challenges of implanted biomaterials are infections, debonding, and lack of minerals at the interface between the dental tissue and biomaterial. These challenges threaten the longevity, durability and effectiveness of the medical procedure. To prevent bacterial infection, dental composites have been embedded with different antimicrobial or therapeutic agents such as silver, quaternary ammonium, copper nanoparticles. To stabilize the bonded interface with minerals (i.e. remineralization), biocomposites have been embedded with therapeutic agents such as fluoride release (e.g., bioactive glasses, glass ionomer cements) and anamorphous calcium phosphates. Despite the efforts and application of different strategies, infection, debonding and lack of minerals at material-tissue interface still a major concern in dentistry. The majority of the dentist practice time (+50%) is invested on re-repairing old problems.

The limitation and challenge with current technologies rely is that every effect (anti microbial or remineralizing) is obtained by a single therapeutic agent or filler. There are no multifunctional fillers tackling both challenges. Having multiple therapeutic fillers in biocomposites increases the complexity of the chemistry, the stability at the bonded interface (biocompatibility) and the user cost.

The herein described novel technology developed a new smart biomaterial with both anti-biofilm and remineralizing effects in a single filler or therapeutic agent. The novel composite was embedded with smart piezoelectric ceramic nanoparticles acting as therapeutic agent. Mastication (chewing) forced excite the piezoelectric filler generating electrical charges at the material surfaces. Electrical charges repelled bacteria (anti infection) and promoted mineralization (grow minerals).

A novel smart biocomposite are developed for dental applications (e.g., sealers) with both antimicrobial and remineralizing effects in a single filler. The therapeutic agent was implanted with piezoelectric nanoparticles. Mastication forces excited the piezoelectric filler generating electrical charges at the material surfaces. Electrostatic forces simultaneously repel biofilms and precipitate new minerals from saturated Calcium solutions from dentinal fluid or blood. This unique approach used one agent to obtain both antimicrobial and self-remineralizing effects, overcoming limitations of current fillers including leaching, alteration of polymerization and use of multiple agents for similar bioactive uses. Thus, this research was performed to elucidate the role of electrical charges on self-mineralization and biofilm modulation advancing the field of infection-free implantable biomaterials.

This technology can be applied to any implanted biomaterial: from titanium implants, to resins. The single therapeutic agent promotes bone growth and prevent any infection. The immediate application was to develop a dental sealer used for endodontic treatments.

Figures 22A, 22B, 22C:
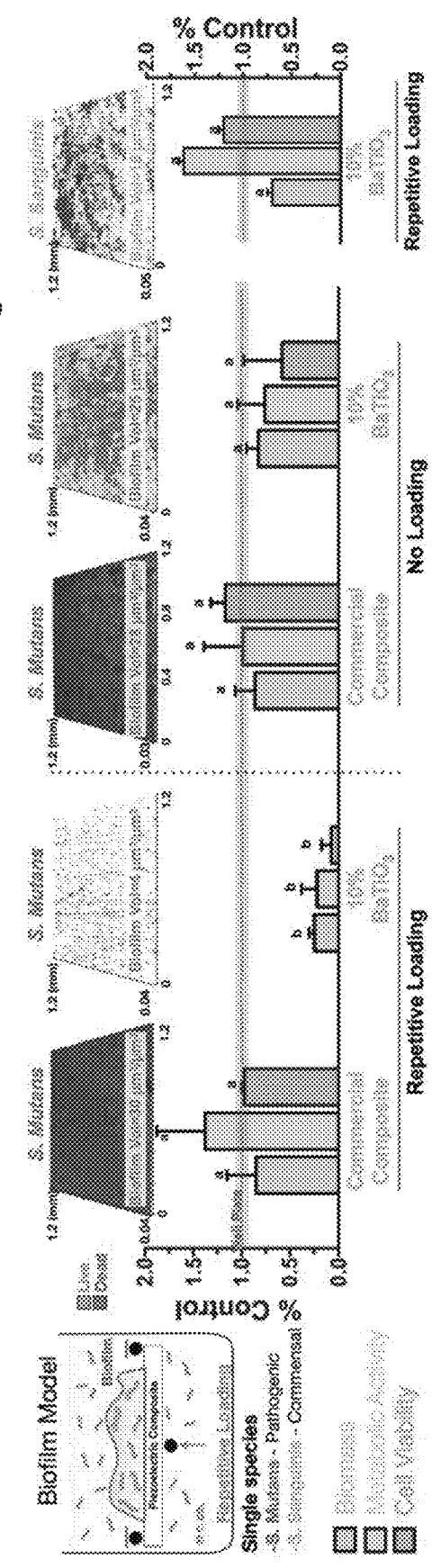
FIG. 22A through FIG. 22C, depicts representative antibacterial properties of piezoelectric resin composites with 10% $BaTiO_3$. (N=7) for each evaluation. Means with different letters are significantly different (p<0.05).
Figures 24A, 24B, 24C, 24D:
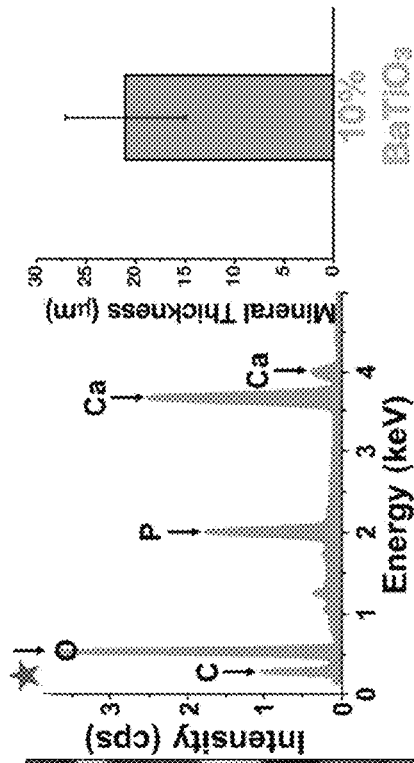
FIG. 24A through FIG. 24D, depicts representative mineralization effects and mineralization properties of piezoelectric composites with 10% BTO.

Piezoelectric nanoparticles also demonstrated antibacterial properties as shown in FIG. 22.

Example 4: Smart Composite With Antibiofilm and Antifungal Therapeutic Effects

Biomaterials have been used for ages to replace damaged tissues and augment body functions. The effective and long-term use of biomaterials inside the body is threatened by the adhesion and proliferation of pathogenic bacteria and fungi growing at the interface between the tissue and the biomaterial (Ahmed W et al., 2019, Mater. Today Bio 2, 100017). Bacteria/fungi forms colonies of microorganisms (i.e., biofilms) that adhere over the surfaces of the biomaterial. Formation of biofilms causes local infections and even implant failure, resulting in death of the patients in the worst case (Xu Q et al., 2017, Nanoscale, 9:19245-19254). Currently, the implant-associated bacterial infections result in more than 100,000 deaths each year in the United States of America (Xu Q et al., 2017, Nanoscale, 9:19245-19254). In dentistry alone, serious oral diseases associated with oral biofilms include caries, periodontitis and oral cancer (Larsen T et al., 2017, Apmis, 125:376-384; Lu M et al., 2019, Food Sci. Hum. Wellness, 8:8-15; Jafer M et al., 2016, J. Contemp. Dent. Pract., 17:337-343; Maddi A et al., 2013, Am. J. Dent., 26:249-254). Direct treatment costs of these dental diseases worldwide were estimated at US$357 billion yearly, corresponding to an average of 4.6% of world health expenditure (Listl S et al., 2015, J. Dent. Res., 94:1355-1361; Righolt A J et al., 2018, J. Dent. Res., 97:501-507). The significance of preventing formation of oral biofilms is extreme important. It has enormous implications for the improvement of health, quality of life and reduction of medical costs (Flemmig T F et al., 2011, Periodontol., 55: 9-15).

The traditional approach to treat and prevent bacterial/fungal related infections is through the use of antibiotics. This class of medicaments utilize chemical compounds to alter and inhibit microorganisms' functions. Unfortunately, the increasingly widespread use (especially the misuse) of antibiotics have led to the dramatic appearance of antibiotic-resistant strains today; more and more infections are caused by microorganisms that fail to respond to conventional treatments (Li B et al., 2018, J. Orthop. Res., 36:22-32). This condition has made antibiotic choices for infection control increasingly limited and more expensive. In the U.S. alone, antibiotic—resistant bacteria cause at least 2 million infections and 23,000 deaths a year resulting in a $55-70 billion per year economic impact (Roberts R R et al., 2009, Clin. Infect. Dis., 49:1175-1184; Antibiotic resistance threats in the United States, 2013, Centers for Disease Control and Prevention). There is an urgent need for developing effective antibiotics-free strategies to minimize the risk of implant-related infection and its potentially life-threatening complications (Wang M et al., 2019, J. Orthop. Transl., 17:42-54). Local strategies for preventing or managing implant-related infection can be achieved throughout biomaterials.

Anti-infective biomaterials have been developed to mitigate infections without the use of antibiotics. A common antimicrobial approach is to modify the biomaterial's surfaces to prevent biofilm formation (Song F et al., 2015, J. Dent. Res., 94:1027-1034) including the creation of anti-biofouling topographies for repulsion and direct killing of microorganisms (Mas-Moruno C et al., 2019, Adv. Healthc. Mater., 8; A Review on Surface Modifications and Coatings on Implants to Prevent Biofilm, 2019, Regen. Eng. Transl. Med.), the coating of the surface with the antimicrobial agents (e.g. silver)(Ahmed W et al., 2019, Mater. Today Bio 2, 100017; Greenhalgh R et al., 2019, Int. Biodeterior. Biodegrad., 136:1-14), the generation of electrical fields/charges to repel microoganisms (Gottenbos B et al., 2001, J. Antimicrob. Chemother., 48:7-13), and photodynamic therapies (use of light to kill microorganisms)(Al-Shammery D et al., 2019, Photodiagnosis Photodyn. Ther.). In dentistry, common antibacterial agents include leachable compounds (e.g., chlorhexidine, triclosan, heparin, antimicrobial peptides), polymerizable monomers (e.g., quaternary ammonium methacrylate's, zwitterion), and filler nanoparticles (e.g. silver, zinc)(Greenhalgh R et al., 2019, Int. Biodeterior. Biodegrad., 136:1-14; Chatzistavrou X et al., 2018, Front. Physiol., 9:103; Jiao Y et al., 2019, Int. J. Oral Sci. 11:1-11). Leachable antibacterial agents are most frequently used despite their potential short-lived efficacy as result of their characteristic burst effect (Zhou X et al., 2019, J. Appl. Polym. Sci., 48180:1-12). Filler particles appear to be effective antibacterial agents, but the color stability of their component metal particles is unfavorable for use in a commercial product (Chan D C et al., 2018, Am. J. Dent., 31:3B-5B). In addition, the biological environment within human body is complex, and antimicrobial materials with additional specific properties (e.g., antifungal or protein-repellent properties) are necessary to achieve better performance in their environments (Jiao Y et al., 2019, Int. J. Oral Sci. 11:1-11).

Fungal infections have increased in incidence in recent decades, often as a result of advanced medical treatments and the increase in the number of immunocompromised patients. *Candida albicans* is still the most frequent cause of fungal infections. However, the use of broad-spectrum antibiotics and antifungal agents for prophylaxis has led to a shift in the epidemiology and etiology of *Candida* and non-*Candida* yeast species infections (Shiang N L et al., 2007, J. Clin. Microbiol., 45:2220-2229). There is a need to find alternative strategies to prevent the formation of biofilms of *Candida*. Very few studies have focused exclusively on antifungal surfaces. However, with increasing recognition of the importance of fungal infections to human health, particularly related to infections at biomaterials, it would seem that the interest in antifungal surfaces is disproportionately low (Coad B R et al., 2014, Biotechnol. Adv., 32:296-307; Giles C et al., 2018, Biotechnol. Adv., 36:264-280). In fact, the limited research into antifungal surfaces is disproportionate to the incidence of potentially fatal fungal infections, and the associated healthcare costs (Coad B R et al., 2014, Biotechnol. Adv., 32:296-307). Medical devices, including dentures, catheters, contact lenses and artificial heart valves, are in constant contact with body fluids, facilitating fungal cell adhesion, followed by their colonization and biofilm formation (Giles C et al., 2018, Biotechnol. Adv., 36:264-280).

Currently, antifungal therapies are scarce and include only four chemical classes of antifungal agents, namely polyenes, triazoles, echinocandins and flucytosine (Chowdhary A et al., 2017, J. Infect. Dis., 216:S436-S444). Moreover, the misuse of antifungal agents over the last two decades has contributed to antifungal resistance development. As result, there is a limitation on the clinical use of antifungal therapies (Perlin D S et al., 2017, Lancet Infect. Dis., 17:e383-e392). Different strategies to prevent fungal biofilm formation over biomaterials include strategies similar to antibacterial such as coatings with anti-fungal agents and anti-biofouling surfaces (Giles C et al., 2018, Biotechnol. Adv., 36:264-280). Common limitations of current technologies include short clinical service life and the need to recharge antifungal agents. Despite those efforts, a universal antifungal mechanism was still not found. There is an urgent need to research on novel strategies to prevent fungal biofilm formation on medical devices (Giles C et al., 2018, Biotechnol. Adv., 36:264-280).

Multifunctional biomaterials aimed to combine the effect of multiple agents (e.g., antibacterial+antifungal) for synergistic effects. Some examples of potential multi-functionality include antibacterial, antifungal, antiviral, protein-repellent (Jiao Y et al., 2019, Int. J. Oral Sci. 11:1-11). This class of biomaterials is realized by combining antiinfection agents into a single formulation. For example, the use of both protein-repellent and antibacterial agents has been shown to result in a much greater reduction in biofilm growth than using a single agent alone. Despite their great potential, biomaterials with multi-agents (e.g., coatings) are expensive with complicated formulations and manufacturing processes that dampen the tunability of physical and mechanical properties for clinical use. In addition, the limitations of single-agents formulation are carried over into the multi-functional system.

The polymicrobial nature of biofilm-associated oral diseases has been increasingly recognized. Clinical data, together with in vivo studies, provide compelling evidence of the importance of cross-kingdom interactions in the severity of diseases (Koo H et al., 2018, PLoS Pathog., 14:1-7). Specially, fungal-bacterial interactions are facilitated by host factors to modify the local microenvironment and promote diseases (Lamont R J et al., 2018, Nat. Rev. Microbiol., 16:745-759; Koo H et al., 2017, Nat. Rev. Microbiol., 15:740-755). Interactions between bacterial and fungal pathogens have shown to have a synergistic enhancement of the virulence of an infectious disease (Falsetta M L et al., 2014, Infect. Immun., 82:1968-1981). Therefore, there is a need for multifunctional biomaterials with combined properties that can combat infections, modulate inflammation, and promote regeneration at the same time (Griffith M et al., 2016, Front. Bioeng. Biotechnol., 4:1-9).

To spearhead this, a new mechanism, described herein, was developed that can prevent the formation of pathogenic biofilms of bacteria and fungi on biomaterials' surfaces. It was revealed for the first time that electrical charges generated by piezoelectric materials enabled the antibacterial and antifungal effects via electrostatic interaction. Piezoelectric biomaterials are well-known to produce electrical charges after stimulated with external mechanical loading (e.g., mastication loading). To show the application of this technology, a dental resin composite incorporated with nanoparticles of piezoelectric materials ($BaTiO_3$) was developed. This unique approach overcame limitations of current anti-infection technologies, such as delivering antibacterial/antifungal therapies with short duration/life, relatively high cost due to complex formulations, and the need to recharge therapies.

This study brought to the biomedical field, especial the orthopedics, dental and medical devices, many impactful innovations including:

1) The use of piezoelectric materials as anti-infective mechanism (antibacterial and antifungal)—For the first time, piezoelectric materials were shown to provide antibacterial and antifungal therapies. These compounds have been successfully used in other biomedical applications (i.e., tissue regeneration, stem cell differentiation)(Rajabi A H et al., 2015, Acta Biomater., 24:12-23). The methods described herein utilized electrical methods to treat biofilms, such as DC voltage (Freebairn D et al., 2013, Expert Rev. Med. Devices, 10:85-103), low AC currents, pulsed electric fields, capacitive coupling treatment, and extremely low-frequency electromagnetic waves (ELF-EMF) are said to be electricidal (Haddad P A et al., 2016, Artif. Organs, 40:804-810). When these methods are used in combination with antibiotics or with host immune responses to create synergistic effect, it was termed a bioelectric effect (Del Pozo J L et al., 2008, Int. J. Artif. Organs, 31:786-795). The herein described technology is a new revelation in the field of antiinfection therapies, since no other technology relies on piezoelectric charges to kill pathogenic microorganisms.

2) Application to many biomedical fields—The use of piezoelectric fillers as antibacterial and antifungal agent has not been investigated previously. This innovation benefits other biomedical fields in the need of new antibacterial-antifungal mechanisms including dental, orthopedics and medical devices. For example, hip or dental implants incorporated treated with piezoelectric coatings, that helped prevent infections. This prevented complications post-surgery and extended the clinical service of implants.

In addition, the herein developed technology could be translated into several areas of dentistry, including endodontics and periodontics. For example, peri-apical periodontitis is a chronic inflammatory lesion caused by bacterial invasion at the pulp via interfacial gaps. Dental cements, posts, etc., were be developed by adding piezoelectric fillers in current formulations without modifying existing properties. The material used nanoparticles incorporated in polymer resins. It was straightforward to translate the powder to other systems (surfaces, other polymer matrixes) without altering the existing properties. The herein described results showed the antibacterial and antifungal effects using two different resin matrixes including BisGMA and PMMA. The anti-infective effect was independent of the matrix, which was a significant benefit of the herein described technology.

3) External activation of antibacterial and antifungal effects—The herein described composite utilized external stimulation to activate the therapeutic effects. The results described herein indicated that either mastication loads, or acoustic waves enabled the antibacterial/antifungal effects. This concept was innovative since current technologies continually deliver therapies without any control after the material is implanted. Controlling the delivery of the therapeutic effects externally, enabled long-lasting effects by metering the doses extending dental restorations' clinical life. Thus, the herein described composite offered long-lasting therapies since piezoelectric materials can produce electrical charge for more than 10 million cycles (~20 years of service).

The herein developed material significantly overcame limitations of the current technologies including 1) The antibacterial/antifungal mechanism did not rely on leaching, ion-diffusion and did not need recharging, 2) A single compound of piezoelectric nanoparticles was utilized to realize the therapies simplifying the material formulation, cost.

Two dental composites incorporated with piezoelectric nanofillers were developed to show the antibacterial and antifungal effect in two independent resin matrixes.

Antifungal Piezoelectric Composite Preparation

A new composite was prepared by mixing Polymethyl methacrylate (PMMA)—material used for dentures—with the piezoelectric nanofillers of $BaTiO_3$. Two important aspects of the technology were shown with this variation: 1) to translate the antifungal mechanism to other material systems (from BisGMA resins to PMMA acrylics using same nanoparticles), 2) to utilize piezoelectric charges to kill and prevent formation of Candida Albicans. This fungal species is relevant to denture-associated stomatitis, and act in synergy with S. mutans to promote serious dental infections.

Samples of PMMA composites with 10% BTO were molded according to the shape needed for mechanical, physical and antifungal characterization and according to the ISO standard for denture base polymers (ISO 20795-1). Commercial PMMA (Bosworth Original Truliner) was purchased and BTO nanoparticles were thoroughly mixed using a planetary mixer. Two groups of samples were evaluated including plain PMMA and PMMA incorporated with 10% of BTO. The basic properties of the PMMA composite including mechanical, electrical charge, DC and water absorption, were measured. Material evaluation of the PMMA piezo-composite was conducted using previously described methods. The yield strength and elastic modulus for the new composite was 65.3 MPa and 2 GPa respectively, which is comparable to PMMA with no additives (70.2 MPa and 3.2 GPa). These values are within the required by the standards and comparable to control PMMA (no fillers) and to the BisGMA composites prepared for the antibacterial model (FIG. 18). The electrical charge was also re-assessed with a maximum 1 pC of charge at the material surfaces, which is comparable to the magnitude obtained for the antibacterial resin.

Antifungal Biofilm Model

To characterize the antifungal performance of piezoelectric charges, a model to grow biofilm of single species of C. albicans on the negative surface of the material was developed based on previous model and existing literature (Nett J et al., 2006, Curr. Opin. Microbiol., 9:340-345). C. albicans biofilms were grown on three different materials. The first group was the PMMA composite with the piezoelectric fillers. The second group was a commercial PMMA material without fillers. The third group was a negative control group consisting of the resin BisGMA-composite (similar material used for antibacterial but tested under fungal species). A fungal strain was obtained (C. albicans CAI4) and inoculated in RPMI 1640 medium at 37° C. A single colony was harvested and incubated to obtain a liquid culture, which was diluted in BHI supplemented with 2% of sucrose to obtain $OD_{600}$=100 equivalent to $10^6$ CFU/mL. A composite sample was then submerged in the liquid culture of fungi. Samples were maintained statically under the liquid culture for 2 hours to allow fungal colonization. After the adhesion time, samples are washed with phosphate-buffered saline (PBS) and refreshed with a new medium. Then, samples were subjected to repetitive loading (2 N and 2 Hz) for the duration of the experiment (48 hours) activating electrical charge generation to enable the antifungal effect (FIG. 23A). The antifungal effects were measured throughout biofilm biomass, metabolic activity, and fluorescent microscopy with live/dead assays.

To evaluate the fungal biofilm-material interaction, the biofilm biomass and metabolic activity were measured. The biofilm were stained with crystal violet (CV). This dye binds to surface molecules and the biofilm extracellular matrix (Feoktistova M et al., 2016, Cold Spring Harb. Protoc., pdb-prot087379). Only adherent cells were stained which means that a biofilm with a higher number of dead cells losing their adherence or less biomass required less dye to stain the biofilm (Wilson C et al., 2017, Res. Rev. J. Eng. Technol., 6). Change on the metabolic activity of the fungi was measured using MTT assay after the 48 hours of stimulation. Finally, fluorescent microscopy (Invitrogen MP, 2009, FilmTracer LIVE/DEAD Biofilm Viability Kit) along with a live/dead assay was be used to image the biofilm and obtain a visual representation of the microorganisms present on the material surface. The results of the microbiological evaluations were normalized by responses from well plates ("positive control") due to the consistency of the material and fungi cultures (Fugolin A P et al., 2019, Acta Biomater.).

Antifungal Effects

Overall, the new piezoelectric PMMA-composite showed antifungal capability evidenced by the reduction of the biomass and metabolic activity compared to commercial PMMA acrylic and BisGMA resins after samples were subjected to mechanical stimulation (FIG. 23B). The amount of fungal biofilm in the commercial PMMA was roughly one order of magnitude higher than that of the piezoelectric PMMA composite after repetitive loading. Moreover, biofilm biomass and metabolic activity of Candida was significant higher when formed on BisGMA resins compared to PMMA acrylics. Fluorescent microscopy revealed a significant increase in red color (dead cells) on PMMA composites after stimulated with mechanical loading compared static (no loaded) samples (FIG. 23D).

The studies described herein also demonstrated the beginning of understanding how different material parameters influence the antibacterial/antifungal effects including the quantity of BTO nano-fillers, and the magnitude/duration of electrical charge. For example, the results described herein also suggested a nanofiller quantity dependence. A decrease on the bacteria metabolic activity on a composite with 1% BTO was observed compared to 10% BTO after charges were activated with repetitive loading. Additional studies are now focused on the optimal amount of filler that enables the antibacterial effects while retaining the physical and improving the mechanical responses.

In summary, a new antibacterial and antifungal technology were developed by the use of piezoelectric materials. It was shown that nanoparticles of piezoelectric fillers can be incorporated in different dental resins and acrylics without affecting the anti-infection effects. For the first time, the advantage of piezoelectric charges as anti-infection mechanism was revealed. This technology can be translated to any biomedical biomaterial as surface treatment (by shot-peening piezoelectric particles onto the surfaces of implants, catheters, medical devices), as filler in composite materials (resins, acrylics, cements, bonding agents). Several biomedical areas in need of anti-infection technologies could be benefited by the herein described technology including dental, orthopedic, medical devices. Studies are also continuing to elucidate the role of piezoelectric charges to repel other relevant pathogenic bacterial/fungal species (gram-positive and -negative), or biofilms with multispecies associated with serious systemic and diseases for different applications.

Overall, the present invention provides novel materials with antibacterial, antifungal and remineralization properties.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composite comprising a polymer matrix and piezoelectric material particles, wherein the piezoelectric material particles are dispersed within the polymer matrix at a ratio of the piezoelectric material particles to polymer matrix of at least 1:100, and wherein the piezoelectric material particles are $BaTiO_3$ (BTO), and wherein the amount of the BTO in the composite is about 10%.

2. The composite of claim 1, wherein the ratio of the piezoelectric material particles to polymer matrix is about 1:10.

3. The composite of claim 1, wherein the composite is a dental composite having an exterior surface, and wherein the concentration of piezoelectric material particles is capable of generating an electric charge at the exterior surface having antimicrobial and remineralizing effects.

4. The composite of claim 1, wherein the composite does not include non-piezoelectric particles comprising silicon.

5. The composite of claim 1, wherein the diameter of BTO particles is about 200 nm.

6. The composite of claim 5, wherein the amount of BTO in the composite is about 10%.

7. A composite comprising a polymer matrix, a chemical photoinitiator and a single filler material comprising piezoelectric particles, wherein the piezoelectric particles are $BaTiO_3$ (BTO), and wherein the amount of the BTO in the composite is about 10%.

8. The composite of claim 7, wherein the diameter of BTO particles is about 200 nm.

9. The composite of claim 7, wherein the composite is a dental composite having an exterior surface, and wherein the concentration of piezoelectric particles is capable of generating an electric charge at the exterior surface having antimicrobial and remineralizing effects.

10. A composite consisting essentially of a polymer matrix, a chemical photoinitiator and filler particles composed of a piezoelectric material, wherein the piezoelectric particles are $BaTiO_3$ (BTO), and wherein the amount of the BTO in the composite is about 10%.

11. The composite of claim 10, wherein the diameter of the BTO filler particles is about 200 nm.

12. The composite of claim 10, wherein the composite is a dental composite having an exterior surface, and wherein the concentration of filler particles composed of a piezoelectric material is capable of generating an electric charge at the exterior surface having antimicrobial and remineralizing effects.

* * * * *